(12) United States Patent
Miyata et al.

(10) Patent No.: US 6,214,207 B1
(45) Date of Patent: *Apr. 10, 2001

(54) METHOD AND APPARATUS FOR MEASURING OXYGEN CONCENTRATION AND NITROGEN OXIDE CONCENTRATION

(75) Inventors: Shigeru Miyata; Noriaki Kondo; Hiroshi Inagaki, all of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/965,512

(22) Filed: Nov. 6, 1997

(30) Foreign Application Priority Data

Nov. 8, 1996 (JP) .................................................. 8-296676

(51) Int. Cl.$^7$ .................................................. G01N 27/41
(52) U.S. Cl. ..................... 205/781; 205/784.5; 205/785; 204/408; 204/425; 204/426
(58) Field of Search .................................. 204/426, 425, 204/408; 205/781, 783.5, 784, 784.5

(56) References Cited

U.S. PATENT DOCUMENTS

| | | |
|---|---|---|
| 4,505,783 | 3/1985 | Mase et al. . |
| 4,722,779 | 2/1988 | Yamada et al. . |
| 4,808,269 | 2/1989 | Kawanabe et al. . |
| 4,824,549 | 4/1989 | Hamada et al. . |

(List continued on next page.)

FOREIGN PATENT DOCUMENTS

| | | |
|---|---|---|
| 0 257 842 | 3/1988 | (EP) . |
| 0 259 093 | 3/1988 | (EP) . |
| 0 488 791 | 6/1992 | (EP) . |
| 0 678 740 | 10/1995 | (EP) . |
| 0 678 740 A1 | 10/1995 | (EP) . |
| 30146 | * 11/1995 | (WO) . |

OTHER PUBLICATIONS

960334, "Thick Film ZrO2 Nox Sensor" pp.:137–142, by Nobuhide Kato, Kunihiko Nakagaki and Noriyuki Ina, (1996) Society of Automotive Engineers, Inc.

*Primary Examiner*—Robert J. Warden, Sr.
*Assistant Examiner*—Kaj K. Olsen
(74) *Attorney, Agent, or Firm*—Morrison & Foerster LLP

(57) ABSTRACT

Using a sole Nox sensor Nox concentration and oxygen concentration are measured accurately. A measurement device for measuring NOx concentration and oxygen concentration comprises an NOx sensor 2 having a first measurement chamber 20 communicating via a diffusion rate regulating layer 4*d* with the gas under measurement and a second measurement chamber 26 communicating with the first measurement chamber 20 via diffusion rate regulating layers 6*d*, 22*d*. A first pump cell 4 and an oxygen concentration measurement Vs cell 6 are formed on the first measurement chamber 20, while a second pump cell 8 is formed on the second measurement chamber 26. Inside of the first measurement chamber 20 is controlled to a constant low oxygen concentration by controlling the first pump current IP1 so that output of Vs cell 6 will equal a reference voltage VC0. By applying a constant voltage across the second pump cell 8 NOx in the second measurement chamber 26 is decomposed to pump out oxygen. Thus NOx concentration and oxygen concentration are measured from the second pump current IP2 and from the first pump current IP1, respectively. During measurement, sensor temperature is detected from the internal resistance of the Vs cell for controlling heater current supplied to heaters 12, 14 to maintain a constant sensor temperature.

24 Claims, 7 Drawing Sheets

U.S. PATENT DOCUMENTS

| | | | |
|---|---|---|---|
| 4,851,103 | * | 7/1989 | Usami et al. .......................... 204/425 |
| 4,875,990 | * | 10/1989 | Kodachi et al. ...................... 204/426 |
| 4,909,072 | * | 3/1990 | Logothetis et al. ................... 204/426 |
| 5,145,566 | * | 9/1992 | Logothetis et al. ................... 204/426 |
| 5,340,462 | | 8/1994 | Suzuki . |
| 5,413,683 | * | 5/1995 | Murase et al. ........................ 204/426 |
| 5,524,472 | | 6/1996 | Hötzel . |
| 5,700,367 | * | 12/1997 | Yamada et al. ........................ 204/408 |
| 5,763,763 | * | 6/1998 | Kato et al. ............................ 204/426 |
| 5,772,965 | * | 6/1998 | Kato et al. .............................. 422/98 |
| 5,780,710 | * | 7/1998 | Murase et al. ........................ 205/781 |
| 5,833,836 | * | 11/1998 | Takami et al. ........................ 205/785 |
| 5,928,494 | * | 7/1999 | Kato et al. ............................ 205/781 |

\* cited by examiner

METHOD AND APPARATUS FOR MEASURING OXYGEN CONCENTRATION AND NITROGEN OXIDE CONCENTRATION

TECHNICAL FIELD OF THE INVENTION

This invention relates to a method and apparatus for measuring the oxygen concentration and the nitrogen oxide concentration using an NOx sensor designed for detecting the concentration of nitrogen oxides as toxious components exhausted from a variety of combustion equipments, such as internal combustion engines.

BACKGROUND

There has hitherto been known a nitrogen oxide concentration measurement device for measuring the concentration of nitrogen oxides (NOx) in exhaust gases of, for example, internal combustion engines, using an NOx sensor in which, as disclosed for example in European publication EP 0678740A1, and SAE paper No.960334 pages 137 to 142, 1996, etc., a first measurement chamber communicating with a measured gas side via first diffusion rate-regulating layer and a second measurement chamber communicating with this first measurement chamber via a second diffusion rate regulating layer are formed of oxygen ion conductive solid electrolyte layers, a first oxygen pumping cell and an oxygen concentration measurement cell are formed on the first measurement chamber by each sandwiching a solid electrolyte layer by a pair of porous electrodes, and in which a second oxygen pumping cell is formed on the second measurement chamber similarly by sandwiching a solid electrolyte layer by another pair of porous electrodes.

In this type of the nitrogen oxide concentration measurement device, the current is caused to flow across the first oxygen pumping cell so that an output voltage from the oxygen concentration measurement cell will be a pre-set constant value for applying a pre-set constant voltage across the second oxygen pumping cell while maintaining a constant oxygen concentration in the first measurement chamber for pumping out oxygen from the second measurement chamber by applying a constant voltage across the second oxygen pumping cell. The NOx concentration in the gas under measurement is detected based on the current value flowing in the second oxygen pumping cell.

It is noted that gas components other than NOx, that is oxygen, carbon monoxide or carbon dioxide, are present in the exhaust gases from the internal combustion engines, that is gas under measurement. In the above-described nitrogen oxide concentration measurement device, the inside of the first measurement chamber is controlled by the first oxygen pumping cell to an extremely low oxygen concentration, while a constant voltage is applied across the second oxygen pumping cell in a direction of pumping out oxygen from the second measurement chamber, on the side of the second measurement chamber into which flows the gas controlled to the low oxygen concentration, thereby decomposing NOx in the gas under measurement into oxygen and nitrogen by the catalytic function of the porous electrode constituting the second oxygen pumping cell and extracting oxygen from the second measurement chamber. The pump current flowing at this time through the second oxygen pumping cell is detected in an attempt for measuring the NOx concentration in the gas under measurement without being affected by the other gas components in the gas under measurement.

For accurate detection of the NOx concentration by the above detection method using the above nitrogen oxide concentration measurement device, each cell needs to be activated by heating the sensor to a pre-set activation temperature, such as 800° C. or higher. Thus, a separate heater is provided for heating the sensor.

SUMMARY OF THE DISCLOSURE

In the course of eager investigation toward the present invention the following problems have been encountered.

Meanwhile, the above-described nitrogen oxide concentration measurement device is used, for instance, for monitoring the state of the NOx catalyst which reduces NOx for suppressing NOx in an internal combustion engine driven at a lean air/fuel ratio, that is with an air/fuel ratio having a proportion of air larger than fuel, thus increasing the NOx component in the exhaust gases, i.e., a so-called lean-burn engine.

Namely, the above-described nitrogen oxide concentration measurement device is used for performing such control in which an NOx sensor is loaded downstream of the NOx catalyst in an exhaust path of the internal combustion engine to measure the NOx concentration for detecting the amount of leakage of NOx from the NOx catalyst, and in which, when the amount of leakage of NOx starts to increase, the air/fuel ratio of the air/fuel mixture supplied to the internal combustion engine is transiently controlled to a fuel-rich air/fuel ratio for discharging unburned gas from a internal combustion engine, with the unburned gas being reacted with NOx accumulated in the NOx catalyst for suppressing emission of NOx.

For realizing this NOx control, a separate air/fuel ratio measurement device for measuring the air/fuel ratio based on the oxygen concentration in the exhaust gas needs to be provided in the internal combustion engine, because the above-mentioned nitrogen oxide concentration measurement device cannot measure the air/fuel ratio of the air/fuel mixture supplied to the internal combustion engine.

For realizing the above-described NOx control, the air/fuel mixture control commmonly carried out in the internal combustion engine in the conventional practice needs to be executed simultaneously. To this end, an NOx sensor and an oxygen concentration sensor (so-called air/fuel ratio Sensor) need to be provided in the exhaust gas system of the internal combustion engine.

It is therefore an object of the present invention to provide a method and a device for measuring oxygen concentration and NOx (nitrogen oxide) concentration only by an NOx sensor without using two sensors, namely a NOx sensor and an air/fuel ratio sensor, particularly, for simplifying the Structure of the detection system of the NOx concentration and oxygen concentration (air/fuel ratio) in implementing the above-described NOx control.

Other objects will become apparent from the entire disclosure of the present invention.

According to a first aspect of the present invention there is provided a method for measuring the oxygen concentration and the nitrogen oxide concentration in a gas under measurement using a NOx sensor having a first measurement chamber, a second measurement chamber and a heater. The first measurement chamber has a first oxygen pumping cell and an oxygen concentration measuring cell and communicating with (the side of) the gas under measurement of a first diffusion rate regulating layer. The first oxygen pumping cell has an oxygen ion conductive solid electrolyte layer sandwiched between porous electrodes. The second measurement chamber has a second oxygen pumping cell having an oxygen ion conductive solid electrolyte layer sandwiched between porous electrodes and communicates with the first measurement chamber via a second diffusion rate regulating layer. The heater is adapted for heating the cells to a pre-set activation temperature. The method includes the step of causing the current to flow in the first oxygen pumping cell so that an output voltage of the oxygen concentration measurement cell will be of a pre-set value for controlling the oxygen concentration in the first measurement chamber to a constant value, the step of applying a constant voltage across the second oxygen pumping cell in a direction of pumping out oxygen out of the first measurement chamber, and the step of measuring the concentration of nitrogen oxide in the gas under measurement based on the value of the current flowing in the second oxygen pumping cell and measuring the oxygen concentration in the gas under measurement based on the value of the current flowing in the first oxygen pumping cell.

In a second aspect according to the first aspect, the amount of the current supplied to the heater is controlled so that the temperature of the oxygen concentration measurement cell in the NOx sensor will be a pre-set target temperature.

In a third aspect according to the second aspect, the measured results of the oxygen concentration and the nitrogen oxide concentration are corrected depending on the deviation from the target value of the temperature of the oxygen concentration measurement cell for compensating the measured results for temperature.

According to a fourth aspect there is provided a device for measuring the oxygen concentration and the nitrogen oxide concentration in a gas under measurement using an NOx sensor similar to the NOx sensor stated in the first aspect. The measurement device includes pump current control means (circuit or module) for causing the current to flow in the first oxygen pumping cell so that an output voltage of the oxygen concentration measurement cell will be of a pre-set value for controlling the oxygen concentration in the first measurement chamber to a constant value, constant voltage application means (circuit or module) for applying a constant voltage across the second oxygen pumping cell in a direction of pumping out oxygen out of the second measurement chamber, nitrogen oxide concentration measurement means (determining circuit or module) for measuring the concentration of nitrogen oxide in the gas under measurement based on the value of the current flowing in the second oxygen pumping cell, and oxygen concentration measurement means (determining circuit or module) for measuring the oxygen concentration in the gas under measurement based on the value of the current flowing in the first oxygen pumping cell.

In a fifth aspect of the present invention according to the fourth aspect, the device further includes temperature detection means (determining circuit or module) for detecting the temperature of the oxygen concentration measurement cell and heater current supplying controlling means for controlling the current supplied to the heater so that the temperature of the oxygen concentration measurement cell as detected by the temperature detection means will be a pre-set target temperature.

In a sixth aspect of the present invention according to the fifth aspect, the device further includes correction means (circuit of module) for temperature-compensating results of measurement of the oxygen concentration and the nitrogen oxide concentration by correcting the results of measurement responsive to deviation from the target temperature of the temperature of the oxygen concentration measurement cell as detected by the temperature detection means.

In a seventh aspect of the present invention according to the fifth or sixth aspect, the temperature detection means detects the temperature of the oxygen concentration measurement cell by detecting the internal resistance of the measurement cell and wherein the heater current supply controlling means controls the amount of the current supplied to the heater so that the detected internal resistance of the oxygen concentration measurement cell will be of a pre-set value corresponding to the target temperature.

In an eighth aspect according to the seventh aspect, in the NOx sensor, the porous electrode on the opposite side of the oxygen concentration measurement cell with respect to the first measurement chamber is closed and part of oxygen in the resulting closed space can be leaked out via a leakage resistance, and wherein the pump current control means causes a small amount of current to flow in the oxygen concentration measurement cell in a direction of pumping out oxygen in the first measurement space into the closed space to control the amount of current flowing in the first oxygen pumping cell so that, as the closed space is caused to function as an internal oxygen reference source, an electromotive force generated across the oxygen concentration measurement cell will be of a constant value, the temperature detection means periodically interrupting connection between the pump current control means and the oxygen concentration measurement cell so that, during such interruption, an amount of current for detecting the internal resistance larger than the small current is caused to flow in the oxygen concentration measurement cell in an opposite direction to the flowing direction of the small current, the internal resistance of the oxygen concentration measurement cell being detected from a voltage generated at this time across the electrodes of the oxygen concentration measurement cell.

In a ninth aspect according to the eighth aspect, the temperature detection means causes the current for detecting the internal resistance to flow in the oxygen concentration measurement cell in one direction, the temperature detection means then causing the current to flow in an opposite direction to the preceding direction of the internal resistance detecting current.

In a tenth aspect according to any one of aspects 4 to 9, in the NOx sensor, the first oxygen pumping cell, oxygen concentration measurement cell and the second oxygen pumping cell are formed of solid electrolyte layers as different thin plates, respectively, the first measurement chamber and the second measurement chamber are made up by laminating the respective solid electrolyte layers each with a small gap in-between with the solid electrolyte layers constituting the first and second oxygen pumping cells facing outwards, the heater including two heater substrates in the form of thin plates being made up of heater substrates with heater wiring embedded therein, the heater substrates being arranged on both sides in the laminating direction of each solid electrolyte layer in the NOx sensor with a pre-set interval in-between for heating the NOx sensor, and wherein the first diffusion layer is arranged in the solid electrolyte layer constituting the first oxygen pumping cell so that the first diffusion layer is disposed at a position opposing a mid position of the heater wiring in the heater substrate.

In an eleventh aspect according to the tenth aspect, the second diffusion rate regulating layer overlaps at least a portion of the first diffusion rate regulating layer in a view where the NOx sensor is projected from the laminating direction of solid electrolyte layers, and wherein the oxygen concentration measurement cell is provided in the vicinity of the second diffusion rate regulating layer.

PREFERRED EMBODIMENTS OF THE INVENTION

In the following preferred embodiments of the invention will be explained.

With the measurement method according to the first aspect, the current is caused to flow in a first oxygen pumping cell so that an output voltage of an oxygen concentration measurement cell in the Nox sensor will be constant thereby controlling the oxygen concentration in the first measurement chamber constant, whilst a constant voltage is applied across the second oxygen pumping cell in a direction of pumping out oxygen from the second measurement cell. Specifically, with this method, the NOx sensor is driven in the same driving direction as that for measuring the NOx concentration using a NOx sensor. At this time, not only is the nitrogen oxide concentration (NOx concentration) measured from the current value flowing in the second oxygen pumping cell, but also is the oxygen concentration in the gas under measurement measured from the current value flowing in the first oxygen pumping cell.

The reason is that the pump current control by controlling the current flowing in the first pumping cell to control the oxygen concentration in the first measurement chamber to a constant value is similar to the operation of measuring the oxygen concentration in the gas under measurement using a universal-range air/fuel mixture sensor having a pumping cell and an oxygen concentration measurement cell in/on a measurement chamber a having limited diffusion of the gas under measurement, such that the current flowing through the first pumping cell is proportionate to the oxygen concentration in the gas under measurement and the oxygen concentration can be measured (derived) from the current value.

Thus, according to the present invention, since the oxygen concentration and the NOx concentration are measured using only the NOx sensor, there is no necessity of providing two sensors, namely an NOx sensor and an air/fuel ratio sensor, in an exhaust gas system of an internal combustion engine, thus simplifying the structure of the control device for reducing the cost.

Moreover, according to the present invention, since the oxygen concentration and the NOx concentration are measured using the sole NOx sensor, the measured results exhibit high correlation as compared to a case where the concentrations are measured using different sensors, that is an oxygen sensor and an NOx sensor. Thus, if the oxygen concentration and the NOx concentration as measured by the inventive method are used, it becomes possible to judge deterioration of the NOx catalyst provided in an exhaust gas pipe of the internal combustion engine with high accuracy.

That is, for grasping the deterioration of the NOx catalyst, it is only necessary to detect to which extent leakage of NOx steadily occurs. To this end, it suffices to compare the control air/fuel ratio and the amount of leakage of NOx for the control air/fuel ratio in order to judge whether or not the amount of leakage of NOx relative to the control air/fuel ratio is within a pre-set allowable range.

That is, in an internal combustion engine, in general, the smaller the air/fuel ratio of the supplied fuel mixture, the smaller is the amount of leakage of NOx and, conversely, the larger the air/fuel ratio, the larger the amount of leakage of NOx. Therefore, an allowable value of the amount of leakage of NOx relative to the air/fuel ratio is pre-set. Then oxygen concentration and NOx concentration are measured simultaneously during the operation of the internal combustion engine, the allowable value of the amount of leakage of NOx corresponding to the measured oxygen concentration, in other words, the air/fuel ratio, is read out, and the measured value of the NOx concentration is checked as to whether or not it is lower than the allowable value and the NOx catalyst is judged to be deteriorated if the measured value of the NOx concentration is in excess of the allowable value.

If, upon making judgment on deterioration of the NOx catalyst, different sensors are used for measuring the oxygen concentration and the NOx concentration, it may be envisaged that an error is caused in detect ion characteristics of the NOx concentration relative to the air/fuel ratio due to, for example, variation in characteristics from sensor to sensor or difference in the degree of deterioration, thus lowering the decision precision in deterioration of the NOx catalyst.

However, even if the individual NOx sensors undergo variation in characteristics, there is no difference in variation of detection accuracy of the NOx and the are/fuel ratio by a sole NOx sensor. Since the oxygen concentration and the NOx concentration in the gas under measurement are measured using the sole NOx sensor according to the present invention, there is no risk of an error being produced in detection characteristics of the NOx concentration relative to the air/fuel ratio, such that deterioration of the NOx catalyst can be judged at high accuracy from (based on) the measured results.

With the measurement method according to the second aspect, the current supplied to the heater provided in the NOx sensor is controlled so that the temperature of the oxygen concentration measurement cell in the NOx sensor will be a pre-set target temperature.

The reason is that, unless the oxygen concentration in the first measurement chamber can be controlled to be constant by current supply control to the first oxygen pumping cell (pump current control), the oxygen concentration cannot be measured correctly, such that, for controlling the oxygen concentration in the first measurement chamber to be constant, it is necessary to hold a constant temperature in the oxygen concentration measurement cell designed to measure the oxygen concentration.

Briefly, the oxygen concentration measurement cell measures the oxygen concentration in the first measurement chamber by setting porous electrode side of the oxygen concentration measurement chamber opposite to the first measurement chamber as a reference oxygen concentration (oxygen partial pressure P1), exploiting the fact that, if a solid electrolyte layer is sandwiched between a pair of porous electrode s, an electromotive force EMF given by the Nernst' equation (1):

$$EMF = A \times T \times \log(P1/P2) \qquad (1)$$

where A is a constant, and T is absolute temperature is generated across the electrodes depending on the oxygen partial pressures P1, P2 of the electrode sides. Therefore, if, with the oxygen concentration measurement cell being at a temperature T of 1000° K and the oxygen concentration in the first measurement chamber being at 1000 ppm, the electromotive force EMF in the oxygen concentration measurement cell is 200 mV, the electromotive force EMF is 160 mV for a temperature T of 800° K. Thus, for controlling the oxygen concentration in the first measurement chamber to be constant, in other words, for correctly measuring the oxygen concentration and the NOx concentration, the temperature in the oxygen concentration measurement cell needs to be kept constant.

In particular, in the above-mentioned universal-range air/fuel ratio sensor hitherto used for measuring the oxygen concentration, the inside of the measurement chamber is controlled by the pump current control so as to be substantially (almost) depleted of oxygen (the state of zero oxygen concentration), it is possible to obtain rather stable temperature characteristics. However, with the NOx sensor, if the inside of the measurement chamber is controlled by the pump current control so as to be substantially depleted of oxygen (the state of zero oxygen concentration), the NOx component in the gas under measurement flowing into the first measurement chamber is decomposed offering a high risk that the NOx concentration (in the gas under measurement) cannot be measured. Therefore, control is made so that a minor amount of oxygen (corresponding to, for example, a low oxygen concentration of 1000 ppm) is left in the first measurement chamber. The result is that the temperature characteristics are significantly lowered as compared to the universal-range air/fuel ratio sensor.

FIG. 10 shows the relation between the output voltage Vs of an oxygen concentration measurement cell and the pump, current Ip flowing in an oxygen pumping cell in a case where the oxygen concentration of the gas under measurement is measured by pump current control employing the conventional universal-range air/fuel ratio sensor, with the oxygen concentration being fixed. As may be seen from this figure, if the pump current Ip is controlled so that the oxygen concentration in a measurement chamber is approximately zero (theoretically on the order of $10^{-9}$ atm), with an output voltage Vs of the oxygen concentration measurement cell being 450 mV, the pump current Ip is changed only by $\Delta$IPA even if the temperature of the oxygen concentration measurement cell is changed from Ta to Tc through Tb, with a current change rate per 1° K being on the order of 2%. However, if the pump current Ip is controlled so that, with an output voltage Vs of the oxygen concentration measurement cell of 150 mV, the oxygen concentration in the measurement chamber is as low as about 1000 ppm, the pump current Ip is significantly changed by $\Delta$IPB when the temperature of the oxygen concentration measurement cell is changed from Ta to Tc through Tb, with the current change rate per 1° K being tens of percent.

Therefore, if, in correctly measuring the oxygen concentration and NOx concentration, using the NOx sensor, as in the present invention, the oxygen concentration in the first measurement chamber is controlled to a lower value of at about 1000 ppm by pump current control in the first oxygen pumping cell, the temperature in the oxygen concentration measurement cell needs to be controlled more correctly to a pre-set temperature.

In contrast, with the measurement method according to the second aspect, the oxygen concentration measurement cell can be maintained at a pre-set constant target temperature by controlling the current supplied to the heater so that the temperature of the oxygen concentration measurement cell in the NOx sensor will be a pre-set target temperature.

Therefore, according to the second aspect, not only can the oxygen concentration and the NOx concentration be measured using the NOx sensor, but also can measurement precision be improved, so that NOx control and decision of NOx catalyst deterioration of the above-mentioned internal combustion engine can be realized more accurately.

With the measurement method of the third aspect, the result of measurement of the oxygen concentration and nitrogen oxide concentration is corrected depending on the temperature deviation of the oxygen concentration measurement cell from the target temperature. Thus, with the present method, even if the temperature of the oxygen concentration measurement cell is changed from the target temperature despite that the temperature of the oxygen concentration measurement cell is controlled by controlling the amount of the current supplied to the heater, the oxygen concentration and the NOx concentration can be temperature-compensated for enabling more accurate measurement of the oxygen concentration and the NOx concentration.

For example, if the driving condition of the internal combustion engine is changed such that the temperature of the exhaust gas as the gas under measurement is drastically changed, there are occasions wherein the NOx sensor temperature is transiently changed responsive to temperature changes in the gas under measurement, such that the temperature of the oxygen concentration measurement cell cannot be sufficiently controlled by heater control. However, with the measurement method of the third aspect, the oxygen concentration and the NOx concentration can be measured accurately even on these occasions.

The measurement device shown in the fourth aspect is a device for implementing the measurement method shown in the first aspect. With this device, pump current control means first causes the current to flow in the first oxygen pumping cell so that the output current of the oxygen concentration measurement cell will be of a constant value in order to control the oxygen concentration in the first measurement chamber to a constant value. On the other hand, the constant voltage application means applies a constant voltage across the second oxygen pumping cell in a direction of pumping out oxygen out of the second measurement chamber. The nitrogen oxide concentration measurement means measures the nitrogen oxide concentration in the gas under measurement based on the current value in the second oxygen pumping cell, while the oxygen concentration measurement means measures the oxygen concentration in the gas under measurement from the current value flowing in the first oxygen pumping cell.

Thus, with the measurement device shown in aspect 4, the measurement method shown in aspect 1 is implemented for measuring the concentration of oxygen and NOx in the gas under measurement, using a sole NOx sensor, thus simplifying the structure of the control device for controlling NOx for an internal combustion engine as described above for reducing its cost while assuring accurate evaluation of the degree of deterioration of the NOx catalyst.

Also, with the measurement device stated in aspect 5, the temperature measurement means detects the temperature of the oxygen concentration measurement cell, while the heater current supplying control means controls the current supplied to the heater provided on the NOx sensor so that the detected oxygen concentration measurement cell temperature will assume a pre-set target temperature. That is, the measurement device shown in aspect 5 is a device for implementing the measurement method stated in aspect 2 and not only can measure the oxygen concentration and the NOx concentration using the NOx sensor but can improve the measurement accuracy for assuring more accurate control of the NOx concentration for the internal combustion engine and more accurate decision of the deterioration of the NOx catalyst.

With the measurement device shown in aspect 6, the correction means corrects the results of measurement of the oxygen concentration and the NOx concentration depending on the deviation from the target temperature of the oxygen concentration measurement cell temperature detected by the temperature detection means. That is, the measurement device shown in aspect 6 is a device for implementing the measurement method stated in aspect 3 and can compensate the measured results of the oxygen concentration and the NOx concentration for temperature, even if the oxygen concentration measurement cell temperature has been changed from the target temperature under the effect of the temperature changes of the gas under measurement despite that the oxygen concentration measurement cell temperature is controlled to the target temperature. This enables more accurate measurement of the oxygen concentration and the NOx concentration.

Although the detection means for detecting the temperature of the oxygen concentration measurement cell may be implemented by a temperature sensor device provided in the vicinity of the oxygen concentration measurement cell, the NOx sensor becomes complex in structure in such case, also offering a difficulty in precisely detecting the temperature of the oxygen concentration measurement cell.

It is noted that the internal resistance of the oxygen concentration measurement cell is varied depending on the cell temperature, such that the internal resistance becomes lower the higher the cell temperature. Therefore, if the internal resistance of the oxygen concentration measurement cell is detected as defined in aspect 7, it becomes possible to detect the cell temperature accurately without necessity of providing a separate temperature sensor device in the NOx sensor, thus enabling simpler and more accurate temperature control.

On the other hand, in case where the internal resistance of the oxygen concentration measurement cell is detected by temperature sensor means, it suffices if a constant voltage is applied across the oxygen concentration measurement cell for sensing the internal resistance for detecting the amount of the current then flowing in the cell, or if a constant current is caused to flow in the oxygen concentration measurement cell for sensing the voltage across both electrodes (or terminals) of the oxygen concentration measurement cell.

For detecting the internal resistance of the oxygen concentration measurement cell, it is necessary to break the connection between the pump current control means and the oxygen concentration measurement cell transiently for stopping the control of current supply to the first oxygen pumping cell by the pump current control means. That is, if the current is supplied to the oxygen concentration measurement cell for detecting the internal resistance, the voltage across both electrodes of the cell ceases to correspond to the oxygen concentration in the first measurement concentration, such that, if the control operation of the pump current control means be continued at this time, the oxygen concentration in the first measurement chamber would be controlled incorrectly. It is therefore desirable to stop the control operation by the pump current control means for precluding such mistaken control operation during measurement of the internal resistance of the oxygen concentration measurement cell.

The oxygen concentration measurement cell measures the oxygen concentration in the first measurement chamber by the electromotive force EMF obtained by equation (1). The oxygen concentration towards one of the paired porous electrodes of the cell which does not contact with the first measurement chamber needs to be a pre-set reference oxygen concentration. To this end, a reference gas with a constant oxygen concentration, such as atmospheric air, may be introduced towards such electrode. However, for introducing the reference gas from outside, it is necessary to provide a gap or conduit for introducing the reference gas in the NOx sensor, thus complicating the NOx sensor structure.

For setting a reference oxygen concentration at a porous electrode on the side of the oxygen concentration measurement cell opposing to the first measurement chamber, it suffices if, in the NOx sensor, the porous electrode on the side of the oxygen concentration measurement cell opposing to the first measurement chamber is closed and part of oxygen in the resulting closed space can be leaked out via a leakage resistance, with the pump current control means causing a small amount of current to flow in the oxygen concentration measurement cell in a direction of pumping out oxygen in the first measurement space into the closed space to control the amount of current flowing in the first oxygen pumping cell so that, as the closed space is caused to function as an internal oxygen reference source, an electromotive force generated across the oxygen concentration measurement cell will be of a constant value, according to aspect 8. In this case, there is no necessity of providing a spacing in the NOx sensor for introducing the reference gas, thus simplifying the structure of the NOx sensor.

For measuring the internal resistance of the oxygen concentration measurement cell by temperature detection means, the temperature detection means periodically interrupts connection between the pump current control means and the oxygen concentration measurement cell so that, during such interruption, an amount of current for detecting the internal resistance larger than the small (or minute) current is caused to flow in the oxygen concentration measurement cell in an opposite direction to the flowing direction of the small current, the internal resistance of the oxygen concentration measurement cell being detected from a voltage generated at this time across the electrodes of the oxygen concentration measurement cell, according to aspect 8.

That is, since the oxygen concentration measurement cell according to the present aspect self-generates the internal oxygen reference source for itself by a small amount of current supplied thereto, a sufficient amount of oxygen is stored in the closed space operating as an internal oxygen reference source, so that, if the internal resistance detection current is caused to flow in the same direction as the small current (for the internal oxygen reference source) flowing direction, the amount of oxygen in the closed space would tend to be excessive, which might result cracks in the NOx sensor due to overcharged oxygen.

Thus, in the measurement device, according to aspect 8, the current for detecting the internal resistance is caused to flow in the opposite direction to the usual small current flowing direction in the oxygen concentration measurement cell for detecting the internal resistance of the oxygen concentration measurement cell from the voltage produced at this time across the electrodes.

Meanwhile, if the current is caused to flow in an oxygen concentration measurement cell, the voltage generated by the cell, that is the voltage across its electrodes, is varied not only with the internal resistance of the oxygen concentration measurement cell but also with the electromotive force generated responsive to the oxygen concentration ratio across the electrodes. However, since the values of the oxygen concentration on each electrode of the oxygen concentration measurement cell (i.e., that in the first oxygen measurement chamber and that in the closed space) are substantially constant by supply of the small amount of current and by current supply control for the first oxygen pumping cell by the pump current control means, the electromotive force directly following the start of current supply of the internal resistance detection current is substantially constant. Therefore, according to the present aspect, the internal resistance of the oxygen concentration measurement cell can be detected without being affected by this electromotive force.

Moreover, if the current for detecting the internal resistance is caused to flow across the oxygen concentration measurement cell in order to detect the internal resistance of the oxygen concentration measurement cell, the latter operates as a pumping cell, such that oxygen is moved in an opposite direction to the current flowing direction responsive to the amount of the supplied current. The result is that the oxygen concentration in the closed space is lowered responsive to the amount of the internal resistance detection current and the current supplying time, such that some interval of time has to elapse after the time of detection of the internal resistance until the oxygen concentration in the closed space is recovered to the reference oxygen concentration by the supply of the small current to permit the oxygen concentration measurement cell to correctly measure the oxygen concentration in the first measurement chamber. Thus, if the control operation for the pump current control means is started directly after the detection of the internal resistance, the oxygen gas concentration and the NOx concentration in the measured gas cannot be measured correctly.

As shown in aspect 9, for reducing the time until it becomes possible to correctly measure the oxygen gas concentration and the NOx concentration after the detection of the internal resistance, the temperature detection means may be designed so as to cause the current for detecting the internal resistance to flow across the oxygen concent rat ion measurement cell in one direction, followed by causing the current to flow in an opposite direction to the preceding direction of the internal resistance detecting current.

That is, if the current for detecting the internal resistance is caused to flow alternately in the oxygen concentration measurement cell during detection of the internal resistance thereof, the state of transient lowering of the electromotive force of the oxygen concentration measurement cell and the oxygen concentration at the respective electrodes of the cell can be quickly recovered to the stable state prior to detection of the internal resistance, thus shortening the time until correct measurement of the oxygen concentration and the NOx concentration after detection of the internal resistance.

Also, according to the present invention, the temperature of one of three oxygen concentration measurement cells of the NOx sensor which is adapted for detecting the oxygen concentration in the first measurement chamber most significantly affecting accuracy in measurement of the oxygen concentration, and the NOx concentration is detected and the amount of the current supplied to the heater is controlled so that the detected temperature will be equal to the target temperature. However, depending on the NOx sensor structure, the temperature of the first oxygen pumping cell or that of the second oxygen pumping cell tends to be deviated from the target temperatures such that sufficient measurement accuracy of the oxygen concentration and the NOx concentration cannot be assured.

For realizing more satisfactory effect proper to the heater current supplying controlling means, it is desirable that, as stated in aspect 10, the first oxygen pumping cell, oxygen concentration measurement cell and the second oxygen pumping cell in the NOx sensor are formed of solid electrolyte layers as different thin plates, respectively, the first measurement chamber and the second measurement chamber are made up by laminating the respective solid electrolyte layers each with a small gap in-between with the solid electrolyte layers constituting the first and second oxygen pumping cells facing outwards. The heater includes two heater substrates in the form of thin plates, being made up of heater substrates with heater wiring embedded therein, the heater substrates being arranged on both sides in the laminating direction of solid electrolyte layers in the NOx sensor with a pre-set interval in-between for heating the NOx sensor. The first diffusion layer is arranged in the solid electrolyte layer constituting the first oxygen pumping cell so that the first diffusion layer is disposed at a position opposing a mid position of the heater wiring in the heater substrate.

That is, if the NOx sensor and the heater are constructed as described above, the solid electrolyte layer provided with the oxygen concentration measurement cell sandwiched between the solid electrolyte layers provided with the first and second oxygen pumping cells, and heater substrates are arranged on both sides thereof in the laminating direction, so that, if the amount of the current flowing in the heater is controlled for controlling the temperature of the oxygen concentration measurement cell, the first and second oxygen pumping cells can be controlled more reliably to close to the target temperatures, while the measured gas flowing from the first diffusion layer into the first measurement chamber can be sufficiently heated by the heater.

The result is that, in the measurement device stated in aspect 10, temperature variations in the respective cells of the NOx sensor can be decreased, while the respective cells are scarcely susceptible to the temperature influence of the gases under measurement, thus further increasing measurement accuracy of the oxygen concentration and the Nox concentration.

According to aspect 11, the second diffusion rate regulating layer overlaps at least a portion of the first diffusion rate regulating layer in a view where the NOx sensor is projected from the laminating direction of solid electrolyte layers, and the oxygen concentration measurement cell is provided in the vicinity of the second diffusion rate regulating layer. The temperature of the NOx sensor and the gases under measurement in the sensor can be controlled more reliably to close to the target temperature, thus improving the oxygen concentration and the NOx concentration.

EXAMPLES

Figure 1:
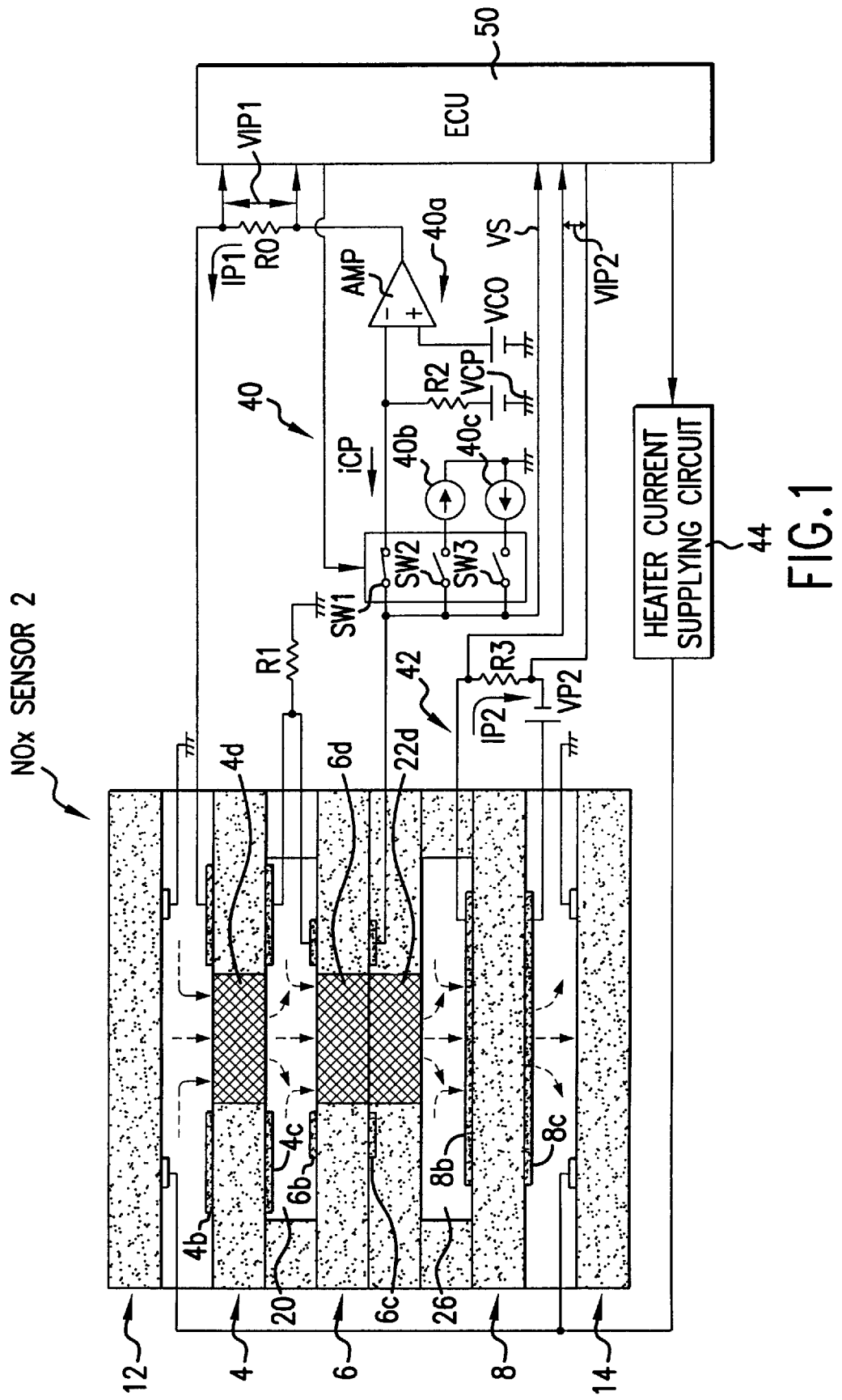
FIG. 1 is a schematic view showing the structure of an overall measurement device for measuring oxygen concentration and the nitrogen oxide concentration according to an embodiment of the present invention.

Referring to the drawings, a preferred embodiment of the present invention will be explained in detail.

Figure 2:
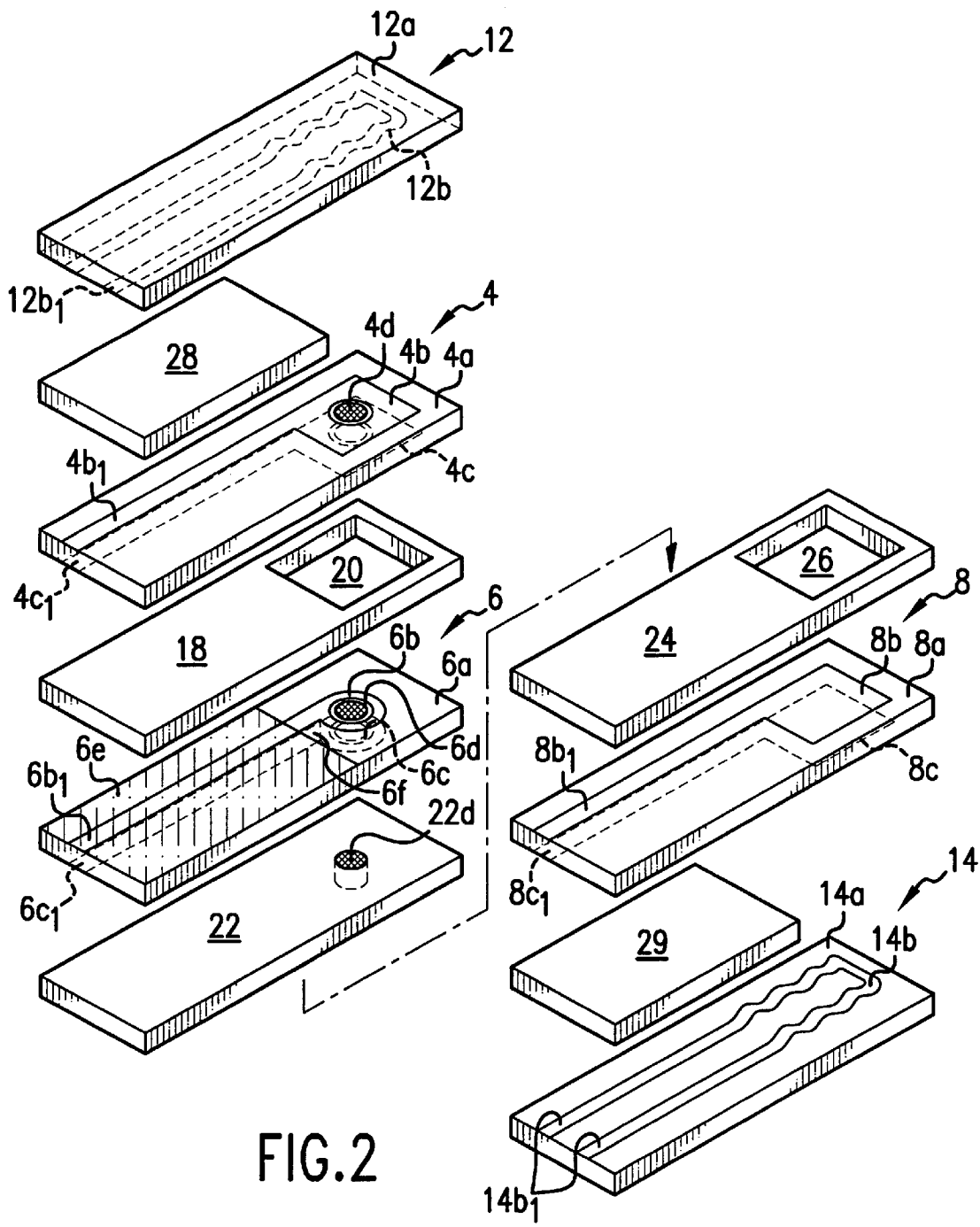
FIG. 2 is an exploded perspective view showing the structure of the NOx sensor according to an embodiment of the present invention.

FIG. 1 shows a schematic structure of the entire device for measuring the oxygen concentration and the NOx concentration of the embodiment of the present invention, while FIG. 2 is an exploded perspective view of an NOx sensor 2 employable for this measurement device.

The measurement device of the present embodiment shown in FIG. 1 includes an NOx sensor 2 and a driving circuit 40 for switching current supply and a current supply path for a first oxygen pumping cell (sometimes referred to herein as "first pumping cell") 4 and an oxygen concentration measurement cell (sometime referred to herein as "Vs cell") 6 constituting the NOx sensor 2 and for detecting a current flowing in the first oxygen pumping cell 4 (sometimes referred to herein as "first pump current") IP1. The measurement device also includes a detection circuit 42 for applying a constant voltage across a second oxygen pumping cell (sometimes referred to herein as "second pump cell") 8 for detecting a current flowing at this time (sometimes referred to herein as the "second pump current") IP2. The measurement device also includes a heater current supplying circuit 44 for supplying a current to a pair of heaters 12, 14 provided in the NOx sensor 2 for heating the cells 4, 6 and 8, and an electronic control circuit 50, sometimes referred to herein as ECU, made up of a microcomputer, for controlling the driving circuit 40 and the heater current supplying current 44 for computing the oxygen concentration and the NOx concentration in the gas under measurement based on detection signals VIP1 and VIP2 from the driving circuit 40 and the detection circuit 42.

Referring to FIG. 2, the first pump cell 4 of the NOx sensor 2 includes a plate-shaped solid electrolyte layer 4a, on both sides of which are formed rectangular porous electrodes 4b, 4c and leads 4b1, 4c1. The solid electrolyte layer 4a is passed through at a mid portion thereof by a circular hole so that the circular hole passes through the center portions of the porous electrodes 4b, 4c. The circular hole is filled (or padded) with a porous filler to form a diffusion rate regulating layer 4d.

The Vs cell 6 is provided with circular porous electrodes 6b, 6c and lead portions 6b1, 6c1 on both sides of the solid electrolyte layer 6a of the same shape as the solid electrolyte layer 4a of the first pump cell 4. The solid electrolyte layer 6a is passed through at a mid portion thereof by a circular hole so that the circular hole passes through the center portions of the porous electrodes 6b, 6c. The circular hole is padded with a porous filler to form a diffusion rate regulating layer 6d.

The center positions of the porous electrodes 6b, 6c of the Vs cell 6 are substantially aligned with the porous electrodes 4b, 4c of the first pump cell 4 on the solid electrolyte layers 6a, 4a, such that, when the Vs cell 6 and the first pump cell 4 are laminated together, the diffusion rate regulating layers 6d, 4d will oppose each other. The circular (annular) porous electrodes 6b, 6c formed on the Vs cell 6 are smaller in size than the rectangular porous electrodes 4b, 4c formed on the first pump cell 4. The front and back surfaces of the Vs cell 6 are coated with alumina insulating films 6e for covering the outer sides of the lead portions 6b1, 6c1 for prohibiting current leakage from these lead portions 6b1, 6c1. Between the lead portions 6b1 and 6c1 is formed a leakage resistance 6f for leaking part of oxygen pumped towards the porous electrode 6c under current supply control as will be explained subsequently to the porous electrode 6b.

The first pump cell 4 and the Vs cell 6, thus formed, are laminated together via a solid electrolyte layer 18 of the same shape as the solid electrolyte layers 4a, 6a. The portions of the solid electrolyte layer 18 facing the porous electrodes 4c, 6b are formed with a rectangular opening which is larger in size than the porous electrode 4c and which operates as a first measurement chamber 20.

On the porous electrode 6c of the Vs cell 6 is layminated a solid electrolyte layer 22 of the same shape as the solid electrolyte layers 4a, 6a. This solid electrolyte layer 22 is formed with a circular opening of the same size as the diffusion rate regulating layer 6d of the Vs cell 6, in register therewith, this circular opening being padded with a porous filler material for forming a diffusion rate regulating layer 22d.

Similarly to the first pump cell 4, the second pump cell 8 is comprised of a plate-shaped solid electrolyte layer 8a, on both sides of which are formed rectangular porous electrodes 8b, 8c and associated lead portions 8b1, 8c1. This second pump cell 8 is laminated on the solid electrolyte layer 22 via a solid electrolyte layer 24 formed identically with the solid electrolyte layer 18. The result is that the rectangular opening bored in the solid electrolyte layer 24 operates as the second measurement chamber 26.

The NOx sensor 2 except for the heaters 12, 14 is fabricated by laminating respective portions together into a unitary body which is then fired at a pre-set temperature.

On both sides of a laminated unit, made up of the first pump cell 4, Vs cell 6 and the second pump cell 8, that is on the outer sides of the first pump cell 4 and the second pump cell 8, are laminated heaters 12, 14 at a pre-set distance (gas) therefrom by spacers 28, 29.

The heaters 12, 14 are provided with heater substrates 12a, 14a of the same shape as the solid electrolyte layers 4a, 6a, . . . , heater wires 12b, 14b formed on the sides of the heater substrates 12a, 14a facing the cells 4, 8 and associated leads 12b1, 14b1. The spacers 28, 29 are arranged over the lead portions 12b1, 14b1 of the heater wires 12b, 14b so that the heater wires 12b, 14b face (oppose) the porous electrodes 4b, 8c of the first pump cell 4 and the second pump cell 8 with a gap in-between, respectively.

The heater substrates 12a, 14a are formed of alumina, whilst the heater wires are formed by screen printing a paste of a mixture of platinum (as a heat resistant metal) powders and alumina on green alumina sheets and firing the resulting set. When fired, the green alumina sheets become heater substrates 12a, 14a and spacers 28, 29. The heaters 12, 14 are unified to the previously fired first and second pump cells 4, 8 from both sides thereof, using a ceramic type adhesive, for completing an NOx sensor 2.

The material making up the solid electrolyte layers 4a, 6a, . . . , may be typified by a solid solution of zirconia and yttria, and a solid solution of zirconia and calcia. In addition, a solid solution of hafnia, a solid solution of perovskite based oxides or a solid solution of trivalent metal oxide, may be used. For the porous electrodes provided on the surfaces of the solid electrolyte layers 4a, 6a, 8a, platinum or rhodium exhibiting catalytic functions or alloys thereof are preferably used. These porous electrodes may be formed by methods typified by a thick film forming method in which a mixture of platinum powders with powders of the same material as that of the solid electrolyte layer is formed into a paste which is then screen-printed on the solid electrolyte layer and fired, or by a coating film forming method through vapor deposition. The diffusion rate regulating layers 4d, 6d and 22d are preferably formed using ceramics having fine through-holes or porous ceramics.

The heater wires 12b, 14b of the heaters 12, 14 are preferably formed of a compound material of ceramics and platinum or platinum alloys, whilst lead portions 12b1, 14b1 thereof are preferably formed of platinum or platinum alloys for lowering the resistance value for reducing electrical losses at the lead portions. The heater substrates 12a, 14a and the spacers 28, 29 may be formed of alumina, spinel, forsterite, steatite or zirconia.

Referring to FIG. 1, the porous electrodes 4c, 6c of the first pump cell 4 and the Vs cell 6 towards the first measurement chamber 20 of the NOx sensor 2 are grounded via resistor R1, while the opposite side porous electrodes 4b, 6b are connected to the driving circuit 40.

The driving circuit 40 includes a controller (control unit) 40a, made up of a resistor R2, having one end supplied with a constant voltage VCP and having its other end connected to the porous electrode 6c of the Vs cell 6 via a switch SW1, and a differential amplifier AMP having a (−) side (inverted) input terminal connected to the porous electrode 6c of the Vs cell 6 via switch SW1 and having its (+) side input terminal supplied with a reference voltage VC0 while having an output terminal connected via a resistor R0 to the porous electrode 4b of the first pump cell 4.

When the switch SW1 is ON, the controller 40a operates as follows:

First, a constant small (minute) current iCP is caused to flow via resistor R2 in the Vs cell 6 for pumping oxygen in the first measurement chamber 20 towards the porous electrode 6c of the Vs cell 6. Since the porous electrode 6c is closed by the solid electrolyte layer 22, while communicating with the porous electrode 6b via leakage resistance 6f, the closed space in the porous electrode 6c is of a constant oxygen concentration by the supply of the minute current iCP, thus operating as an internal reference oxygen source.

If the side of the porous electrode 6c of the Vs cell 6 operates in this manner as an internal reference oxygen source, an electromotive force is generated in the Vs cell 6 in an amount proportionate to the ratio of the oxygen concentration in the first measurement chamber 20 to that of the inner oxygen reference source, with the voltage Vs of the porous electrode 6c becoming a voltage corresponding to the oxygen concentration in the first measurement chamber 20. Since this voltage is supplied to the differential amplifier AMP, the latter outputs a voltage corresponding to the difference between the reference voltage VC0 and the input voltage (VC0−input voltage). This output voltage is impressed to the porous electrode 4b of the first pump cell 4 via resistor R0.

The result is that the first pump current IP1 flows through the first pump cell 4. This first pump current IP1 controls the electromotive force generated in the Vs cell 6 to be a constant voltage, that is controls the oxygen concentration in the first measurement chamber 20 to be a constant concentration. Namely, the controller 40a acts as a pump current control means to control the oxygen concentration in the first measurement chamber 20 so as to bring that in the first measurement chamber constant when the gas under measurement flows into the first measurement chamber 20 via the diffusion rate regulating layer 4d.

Meanwhile, the oxygen concentration in the first measurement chamber 20, thus controlled, is set to a low oxygen concentration, for example, an oxygen concentration of the order of 1000 ppm, which precludes the possibility of decomposition of the NOx components in the gas under measurement in the first measurement chamber 20. Thus, the reference voltage VC0 governing this oxygen concentration is set to a value on the order of 100 mV to 200 mV. A voltage VIP1 across both terminals of the resistor R0, provided between the output of the differential amplifier AMP and the porous electrode 4b for detecting the first pump current IP1, is entered to the ECU 50 as a detection signal for the first pump current IP1.

The driving circuit 40 is provided not only with the above-mentioned controller 40a, but also with a constant current circuit 40b connected via switch SW2 to the porous electrode 6c of the Vs cell 6 for causing a constant current to flow between the porous electrodes 6b and 6c in an opposite direction to the flowing direction of the small current iCP and with a constant current circuit 40c connected via switch SW3 to the porous electrode 6c of the Vs cell 6 for causing a constant current to flow between the porous electrodes 6b and 6c in the same direction as the flowing direction of the small current iCP.

These constant current circuits 40b, 40c operate for detecting the internal resistance RVS of the Vs cell 6. The voltage Vs of the porous electrode 6c is entered to the ECU 50 for enabling the internal resistance RVS of the Vs cell 6 to be detected by the ECU 50 by the supply of this constant current. The constant currents caused to flow by the constant current circuits 40b, 40c are of the same magnitude, although the current flowing directions are opposite to each other. This current value is larger than the small current iCP supplied via the resistor R2 to the Vs cell 6.

The switches SW1 to SW3, connected between the controller 40a, constant current circuits 40b and 40c, on the one hand, and the porous electrode 6c of the Vs cell, on the other hand, are turned on and off by a control signal from the ECU 50 for measuring the oxygen concentration and the NOx concentration. During normal operation, only the switch SW1 is turned on to operate the controller 40a. The switch SW1 is turned off only for detecting the internal resistance RVS of the Vs cell 6, while the switches SW2, SW3 are controlled to be turned on sequentially (alternately).

On the other hand, a constant voltage VP2 is impressed across the porous electrodes 8b, 8c of the second pump cell 8 of the NOx sensor 2 via a resistor R3 as constant voltage impressing means of the detection circuit 42. The constant voltage VP2 is impressed in such a direction that the porous electrodes 8c and 8b assume positive and negative, respectively, so that, in the second pump cell 8, the current will flow from the porous electrode 8c towards the porous electrode 8b for pumping oxygen in the second measurement chamber 26 to outside. Moreover, the constant voltage VP2 is set to a voltage capable of decomposing NOx components in the gas under measurement in the second measurement chamber flowing from the first measurement chamber 20 via diffusion rate regulating layers 6d, 22d for pumping out its oxygen component, such as, for example, 450 mV The resistor R3 operates for converting the second pump current IP2 flowing in the second pump cell 8 on impression of the constant voltage VP2 into a voltage VIP2 which is entered as a detection signal for the first pump current IP2 to the ECU 50.

In the above-described oxygen concentration and nitrogen oxide concentration measurement device of the present embodiment, if the switch SW1 in the driving circuit 40 is turned on, while the switches SW2 and SW3 are turned off, the oxygen concentration in the first measurement chamber 20, into which the gas under measurement flows via the diffusion rate regulating layer (first diffusion rate regulating layer) 4d, is controlled to a constant oxygen concentration by the operation of the controller 40a. The gas under measurement in the first measurement chamber 20, thus controlled to a constant oxygen concentration, flows into the second measurement chamber 26 via diffusion rate regulating layers (second diffusion rate regulating layers) 6d, 22d. Thus, the first pump current IP1 flowing in the first pump cell 4 is changed responsive to the oxygen concentration in the gas under measurement, such that the first pump current IP1 flowing across the first pump cell 4 varies in accordance with the oxygen concentration in the gas under measurement, whilst the second pump current IP2 flowing across the second pump cell 8 varies in accordance with the NOx concentration in the gas under measurement. The ECU 50 reads detection signals VIP1 and VIP2 representing the currents IP1 and IP2 to execute pre-set processing (computing) operations for measuring the oxygen concentration and the NOx concentration in the gas being measured.

For assuring high measurement accuracy of the respective concentrations, the temperatures in the cells 4, 6 and 8, in particular the temperature of the Vs cell 6 detecting the oxygen concentration in the first measurement chamber 20, need to be controlled to be constant. To this end, the amount of the current supplied to the heaters 12, 14 from the heater current supplying circuit 44 needs to be controlled so that the temperature of the Vs cell 6 will be equal to the target temperature. Thus, in the present embodiment, the ECU 50 changes over the states of the switches SW1 to SW3 between the on and off states for detecting the temperature of the Vs cell 6 from its internal resistance RVS and the amount of the current from the heater current supplying circuit 44 to the heaters 12, 14 is controlled so that the detected value of the internal resistance RVS will be of a constant value (that is so that the temperature of the Vs cell 6 will be a target temperature).

The control operation executed by the ECU 50 for temperature control and concentration control will now be explained by referring to the flowchart shown in FIGS. 3 and 4.

Figure 3:
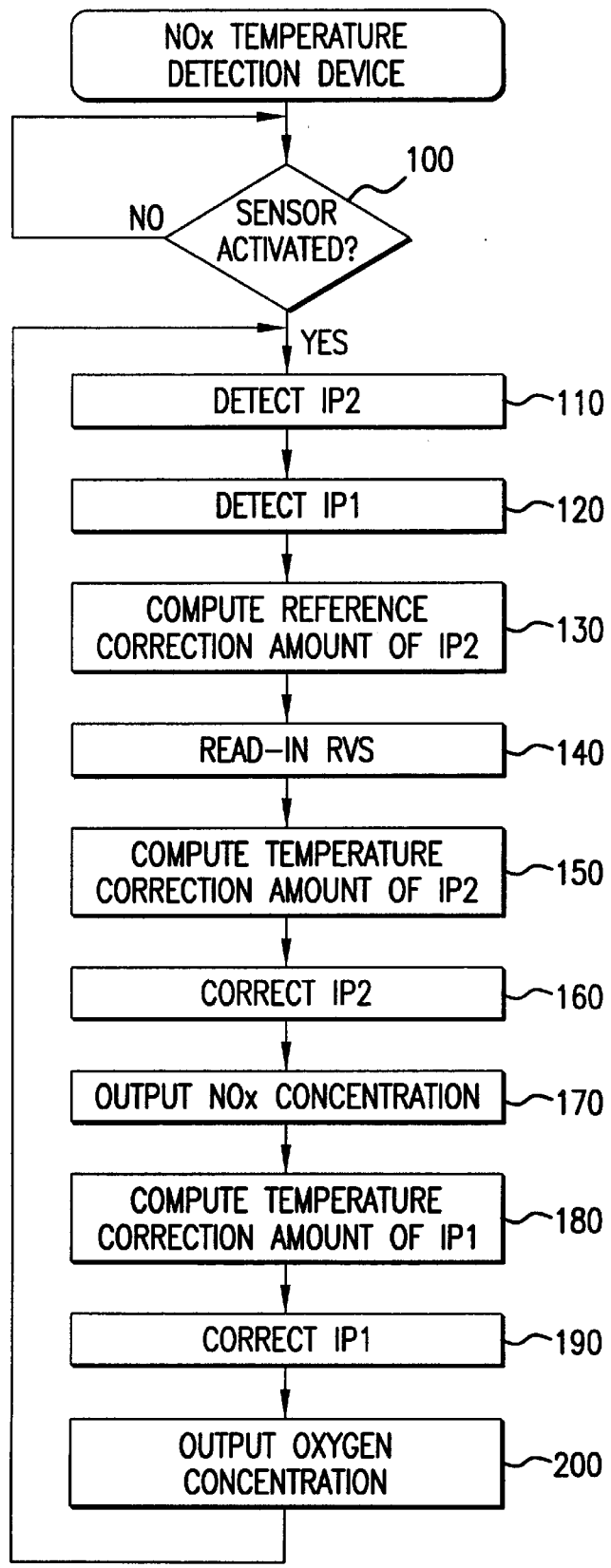
FIG. 3 is a flowchart illustrating processing for measuring oxygen concentration and NOx concentration repeatedly executed by an ECU according to an embodiment of the present invention.
Figure 4:
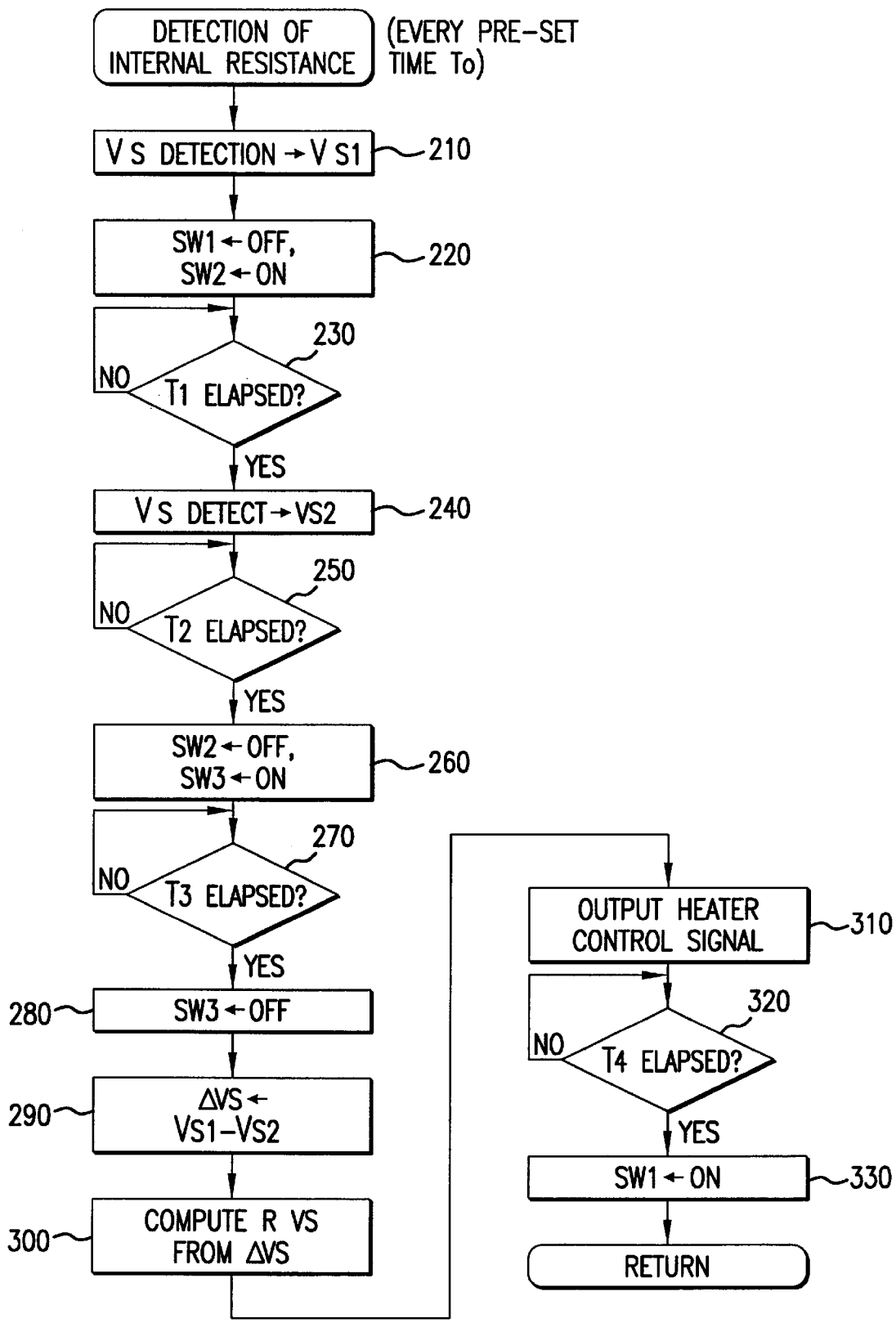
FIG. 4 is a flowchart illustrating an internal resistance detection processing executed as interrupt processing every pre-set time period in the ECU according to the embodiment of the present invention.

FIG. 3 shows the processing for measuring the oxygen concentration and the NOx concentration repeatedly carried out in the ECU 50, while FIG. 4 shows internal resistance detection processing executed within the ECU 50 as interrupt handling (processing) every pre-set time T0, such as 1 second, for detecting the internal resistance RVS of the Vs cell 6 for controlling the current conduction to the heaters 12, 14.

Referring to FIG. 3, after starting the measuring device, the oxygen concentration and NOx concentration measurement processing first conducts the current through the heaters 12, 14 at step S100 in order to judge whether or not the NOx sensor 2 has become activated by current supply to the heaters 12, 14 for awaiting activation of the NOx sensor 2 by way of activation judgment processing.

Figure 5:
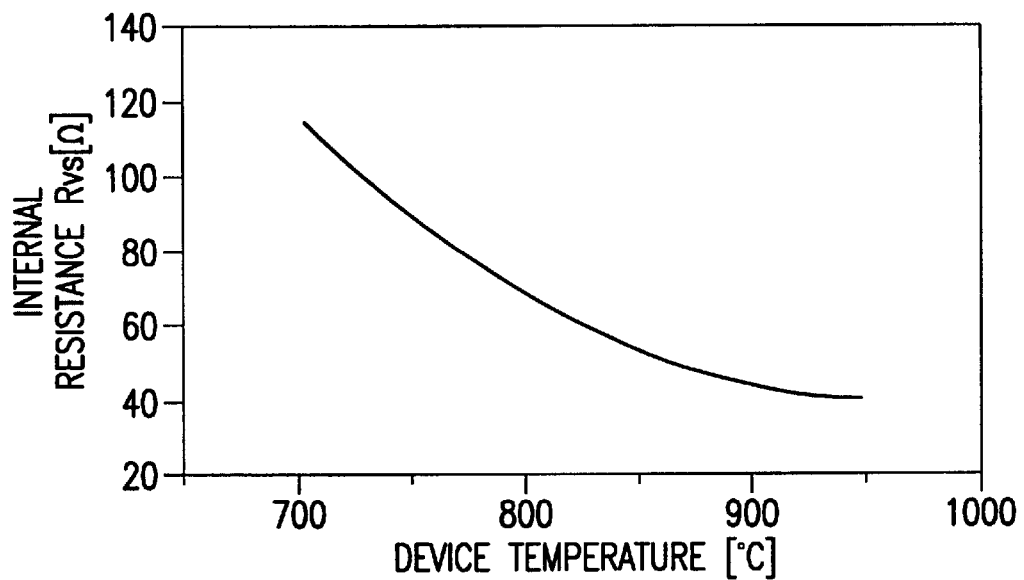
FIG. 5 is a chart showing the relation between the device temperature and the internal resistance of an oxygen concentration measurement cell.

This activation judgment processing is executed by judging whether Or not the internal resistance RVS of the Vs cell 6 as detected by internal resistance detection processing as later explained has become not higher than a pre-set activation judgment value. That is, since the internal resistance of the Vs cell 6 is decreased with rise in the device temperature and with activation of the Vs cell 6, as shown in FIG. 5, the step S100 judges whether or not, after starting current supply to the heaters 12, 14, the internal resistance RVS of the Vs cell 6 has become not higher than a pre-set activation judgment value in order to judge whether or not the device temperature has reached a pre-set activation temperature.

Immediately after starting of the measurement device, the switch SW1 in a driving circuit 40 is controlled to be turned on, while the switches SW2, SW3 are controlled to be turned off, by the initializing processing, not shown. Until the time the NOx sensor 2 rises to near the activation temperature, the operation of the differential amplifier AMP in the driving circuit 40 is halted by the activation judgment processing at S100. The reason is that, as long as the NOx sensor 2 is not activated, the internal resistance RVS in the Vs cell 6 is large, so that the voltage (potential) Vs of the porous electrode 6c entered to the differential amplifier AMP becomes excessive, such that, if the differential amplifier AMP is actuated, an excess current flows through the first pump cell 4.

If the NOx sensor 2 is judged to have been activated at S100, processing proceeds to step S110 to read in a detection signal VIP2 entered from the resistor R3 of the detection circuit 42, to execute processing as a nitrogen oxide concentration measurement means for detecting the second pump current IP2. At the next step S120, the detection signal VIP1 entered via resistor R0 of the driving circuit 40 is read to execute processing as oxygen concentration measurement means for detecting the first pump current IP1.

At the next step S130, a reference correction amount for the second pump current IP2 is calculated based on the detected first pump current IP1.

Figure 6:
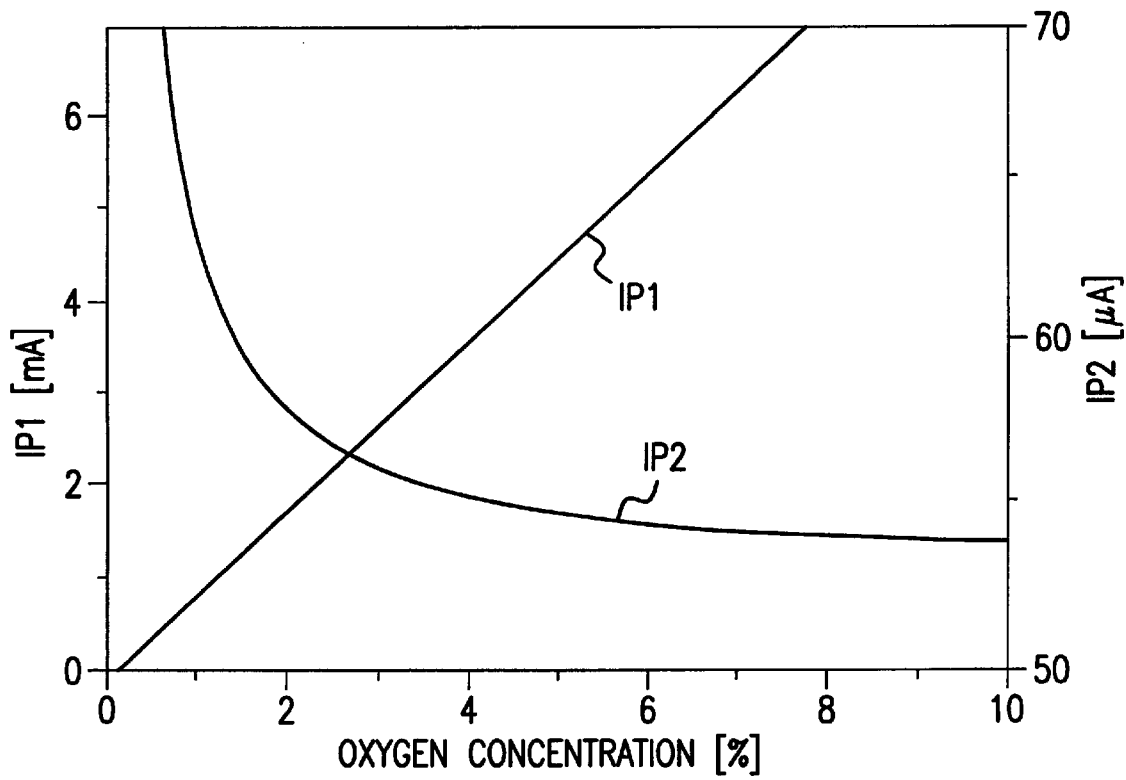
FIG. 6 is a chart showing the relation between the oxygen concentration of the gas under measurement free of NOx and the first and second pump currents.

That is, in the present embodiment, not only NOx but also oxygen in the gas being measured flows into the second measurement chamber 26 because the oxygen concentration in the first measurement chamber 20 is controlled towards a low oxygen concentration side for evading possible decomposition of the NOx components in the gas being measured in the first measurement chamber 20 by pump current control by the driving circuit 40. Thus, although the second pump current IP2 varies in accordance with the NOx concentration in the gas being measured, it is also influenced by the oxygen concentration in the gas being measured. As may be seen from FIG. 6 showing typical results of measurement of the first pump current IP1 and the second pump current IP2 when the device is actuated using a test gas not containing NOx as the gas being measured, the first pump current IP1 varies with a constant gradient in keeping with the oxygen concentration in the gas under measurement, while the second pump current IP2 varies also under the influence of the oxygen concentration in the gas under measurement.

Thus, in the present embodiment, in order for the second pump current IP2 to correspond only to the NOx concentration in the gas being measured, the value of the second pump current IP2 corresponding to the oxygen concentration obtained on measuring the gas under measurement free of NOx as described above is previously stored in a recording medium, such as ROM, as an offset value for correcting the second pump current IP2, the oxygen concentration in the gas under measurement is detected from the first pump current IP1 and the offset value corresponding to this oxygen concentration is read out from the previously stored offset value data for setting as the above-mentioned reference correction amount.

For calculating this reference correction amount, a map having stored therein an offset value associated with the first pump current IP1 (reference correction amount) is used, and this map is retrieved using the first pump current IP1 as a parameter, for directly finding a reference correction amount from the first pump current IP1.

When the reference correction amount has been calculated in this manner, the processing proceeds to step S140 for reading in the internal resistance RVS of the Vs cell 6 obtained by the internal resistance detection processing as later explained. At the next step S150, the temperature correction amount for the second pump current IP2 is calculated based on the read value of the internal resistance RVS.

That is, in the present embodiment, the current supplied to the heaters 12, 14 is controlled so that the detected value of the internal resistance RVS of the Vs cell 6 will assume a pre-set value, in other words, so that the temperature of the NOx sensor 2 will assume a pre-set target temperature. However, if the temperature of the gas under measurement is changed abruptly, the temperature control cannot follow up the temperature changes in the gas under measurement, such that the temperature of the NOx sensor 2 may be occasionally changed based on changes in the temperature of the measured gas.

Figure 7:
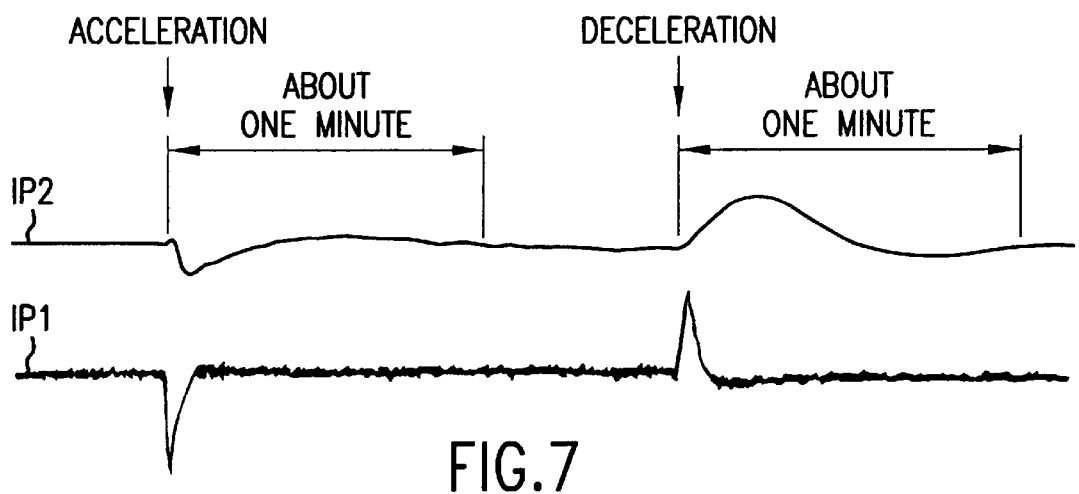
FIG. 7 is a timing chart showing changes in the first and second pump currents caused by changes in the exhaust gas temperature during acceleration and deceleration of an internal combustion engine.

FIG. 7 shows an example of measured results of temperature changes in the NOx sensor 2 when the NOx sensor 2 is mounted in an exhaust gas pipe of an internal combustion engine and the measurement device of the present embodiment is in operation for measuring the NOx concentration in the exhaust gas of the internal combustion engine. As may be seen from FIG. 7, if, in the measurement device of the present embodiment, the exhaust gas temperature is transiently decresed with an increased amount of air intaken upon acceleration of the internal combustion engine, or if the exhaust gas temperature is transiently raised with a decreased amount of air taken upon deceleration thereof, both the first pump current IP1 and the second pump current IP2 are changed under the influence of such temperature changes despite temperature control as later explained. In particular, it takes time as long as about one minute until the second pump current IP2 resumes its stable state. The reason is that, if the second pump current IP2 is affected by the exhaust gas temperature such that the oxygen concentration in the first measurement chamber 20 is deviated from the target concentration, it takes time until the oxygen concentration is reset to its target temperature.

Figure 8:
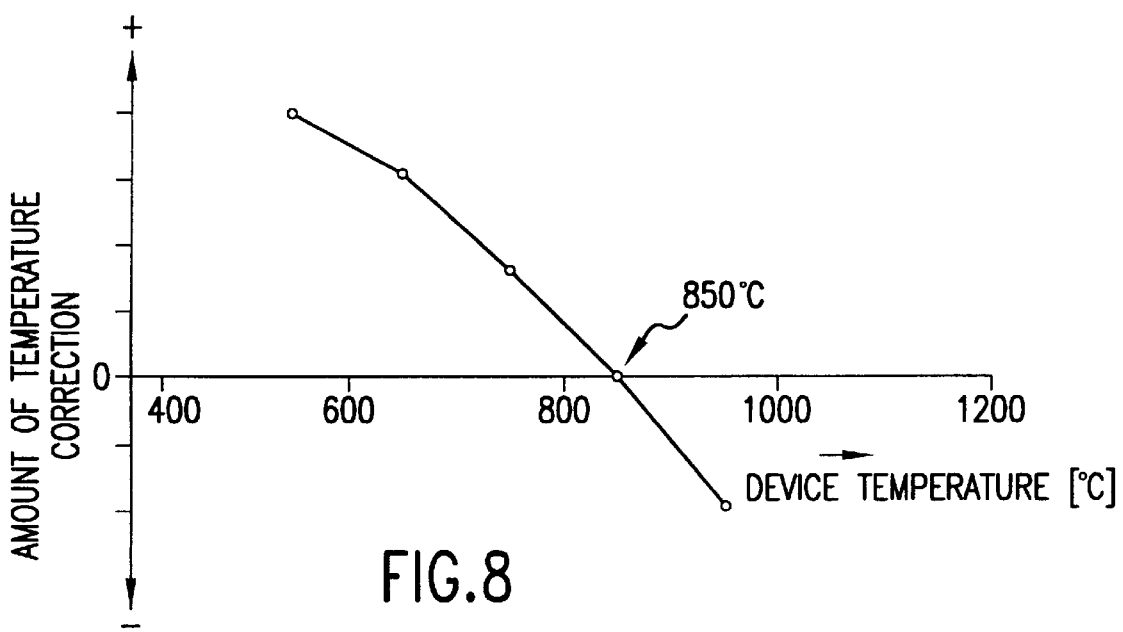
FIG. 8 is a chart showing an example of a map used for determining the amount of temperature correction for the second pump current.
Figure 9:
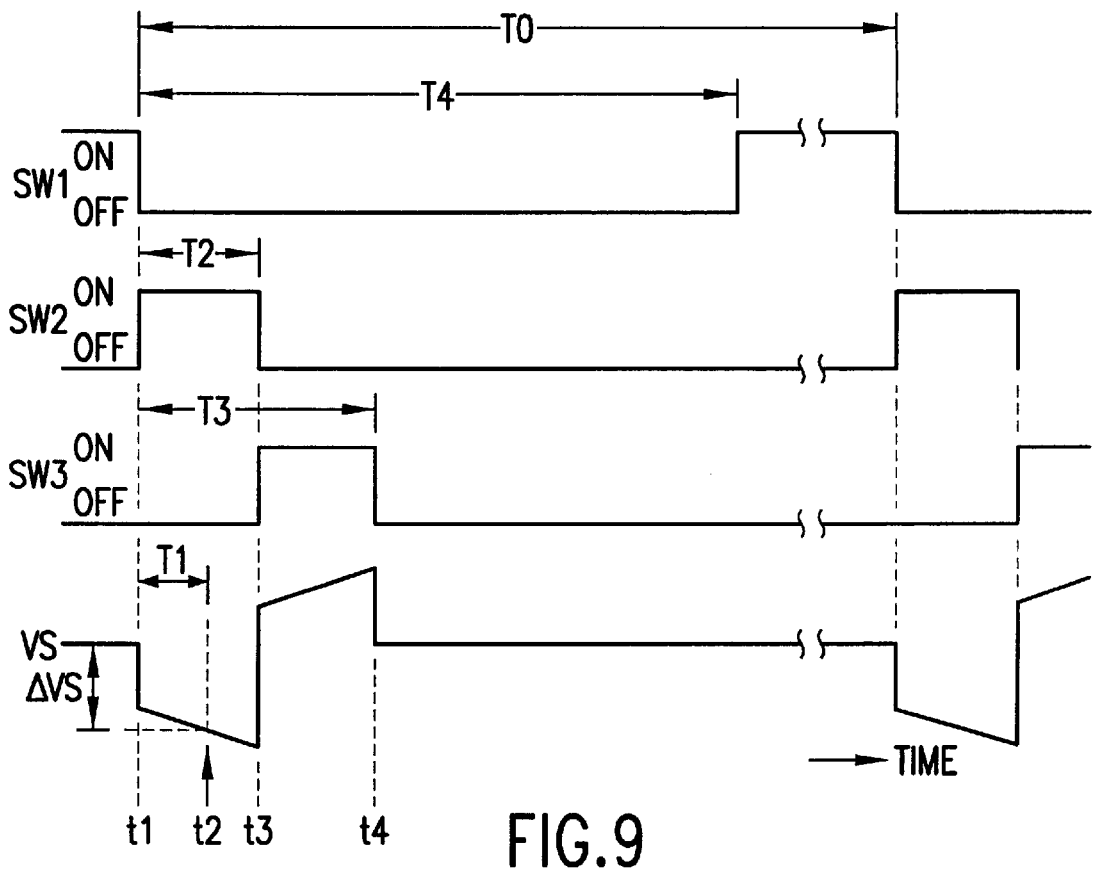
FIG. 9 is a timing chart illustrating the operation during internal resistance detection processing shown in FIG. 4.
Figure 10:
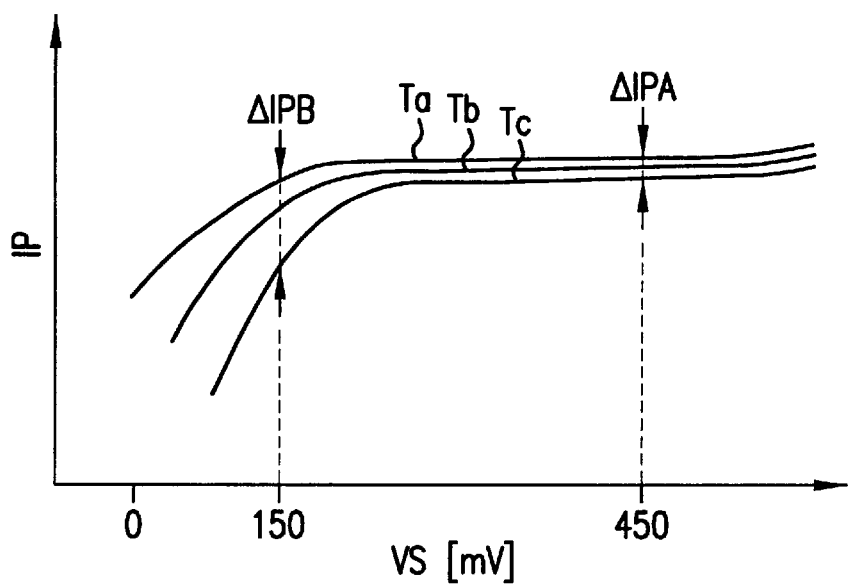
FIG. 10 is a graph illustrating temperature characteristics of oxygen concentration obtained by pump current control in an universal range air/fuel ratio sensor

Thus, in the present embodiment, the temperature of the Vs cell 6 is obtained from the internal resistance RVS of the Vs cell 6 and, using a map for calculating the amount of temperature correction shown for example in FIG. 8, for enabling correct measurement of the NOx concentration from the second pump current IP2 even if the temperature of the measured gas is changed acutely.

The map shown in FIG. 8 is designed for finding the amount of temperature correction from the device temperature of the Vs cell 6. However, if a map is prepared beforehand for calculating the amount of temperature correction having the internal resistance RVS of the Vs cell 6 as a parameter, the amount of temperature correction can be obtained directly from the internal resistance RVS without the necessity of recalculating (or recovering) the internal resistance RVS into temperature. It is also possible to pre-set a map having an offset between the device temperature and the target temperature (850° C. in FIG. 8) in order to find the amount of temperature correction from the deviation from the target value of the device temperature. Alternatively, it is possible to previously set a map having an offset between the internal resistance RVS and a target resistance value associated with a target temperature as a parameter in order to find the amount of temperature correction from the offset (deviation) of the value of the internal resistance RVS from the target resistance value.

If the amount of temperature correction is found at step S150, proceeds transfers to step S160 where the amount of reference correction and the amount of temperature correction are summed to the second pump current IP2 detected at step S110 for correcting the second pump current IP2. At the next step S170, the as-corrected second pump current IP2 is outputted to an external device, such as an engine controlling device, as the results of measurement of the NOx concentration.

Next, the amount of temperature correction for the first pump current IP1 is calculated based on the internal resistance RVS read at step S140. At the next step S190, the first pump current IP1 detected at S120 is corrected, using the calculated amount of temperature correct ion and, at the next step S200, the corrected value of the first pump current IP1 is outputted to an electronic equipments, as a result of measurement of the oxygen concentration, before proceeding again to S110.

Meanwhile, the processing at S180 and S190 is the processing for associating the first pump current IP1 with the oxygen concentration in the exhaust gas so that the first pump current IP1 will be associated with the oxygen concentration in the gas under measurement without being influenced by temperature changes in the NOx sensor 2. At S180, the amount of temperature correction for the first pump current IP1 is found using the pre-set map, as in S150 above.

In the present embodiment, the processing of S150, S160, S180 and S190, carried out for correcting the second pump current IP2 associated with the NOx concentration and for correcting the first pump current IP1 associated with the oxygen concentration in accordance with the temperature of the Vs cell 6, corresponds to the correction means of the present invention.

The foregoing description of the present embodiment has been made on the condition that, in the measurement operation of the oxygen concentration and the NOx concentration, the reference correction amount for correcting the second pump current IP2 in accordance with the oxygen concentration in the gas under measurement based on the first pump current IP1 and the reference correction amount for correcting the second pump current IP2 in accordance with the temperature in the Vs cell 6 are separately found to correct the second pump current IP2. However, the correction amount for correcting the second pump current IP2 may be found in accordance with the oxygen concentration in the gas under measurement and the temperature in the Vs cell 6 by setting maps for calculating the reference correction amount from one Vs cell temperature to another and by switching between the maps used for calculating the reference correction amount depending on every Vs cell temperature. Alternatively, a two-dimensional map for calculating the correction amount may be pre-set, using the first pump current IP1 and the temperature of the Vs cell 6 (or the internal resistance RVS) as parameters in order to find the correction amount for the second pump current IP2 using this map.

The processing for detecting the internal resistance shown in FIG. 4 will be now explained. Meanwhile, this processing for detecting the internal resistance has not only the function of temperature detection means for detecting the internal resistance RVS of the Vs cell 6, but also the function of the heater current supply control means for controlling the amount of current supplied to the heaters 12, 14 through the heater current supplying circuit 44 based on the results of detection.

As shown in FIG. 4, if this processing is started, the voltage Vs on the porous electrode 6c of the Vs cell 6 is read at S210 and set as a basic detection voltage VS1 of the Vs cell 6. At the next step S220, the switch SW1, which has been on for measuring the concentration, is turned off, while the switch SW2 connected to the constant current source 40b is turned on for causing the constant current to flow in a reverse direction to the flowing direction of the small current in the VP cell 6, that is in a direction of pumping, oxygen from the closed space operating so far as an internal oxygen source towards the first measurement chamber 20.

At the next step S230, it is judged, whether or not a preset set time T1, such as 60 μsec, has elapsed after starting the detection processing, to wait until lapse of the pre-set time T1. If the pre-set time T2 has elapsed, the voltage on the porous electrode 6c of the Vs cell 6 is read at step S240 to set the voltage Vs thus read as a resistance detection voltage VS2 of the Vs cell 6.

If the resistance detection voltage VS2 is thus set, the processing proceeds to step S250 for judging whether or not the pre-set time T2, such as 100 μsec, has elapsed since start of the detection processing, to wait until lapse of the pre-set time T2. If the pre-set time T2 has elapsed, the detection processing is started at S260. The switch SW2, which has been on for the pre-set time T2, is turned off, while the switch SW3, connected to the constant current source 40c, is turned on, for causing the constant current to flow into the Vs cell 6 in the same direction as the flowing direction of the small current iCP, that is in a direction of pumping oxygen in the first measurement chamber 20 towards the closed space.

If the switch SW3 is turned on in this manner, the processing proceeds to step S270 to judge whether or not the pre-set time T3, such as 200 μsec, has elapsed after start of the detection processing, to wait until lapse of the pre-set time T3. If the pre-set time T3 has elapsed, the switch SW3 is turned off at S280. This turns all of the switches SW1 to SW3 in the driving circuit 40 off.

At the next step S290, an offset (deviation) ΔVs (=VS1−VS2) between the basic detection voltage VS1 as set directly after the start of the detection processing and the resistance detection voltage VS2 as set after the lapse of the pre-set time T1 is obtained. At step S300, the internal resistance RVS of the Vs cell 6 is calculated from this offset ΔVs followed by proceeding to S310. The method for calculating the internal resistance RVS in the present embodiment will be explained subsequently.

A step S310, processing as heater current supply control means is carried out, in which a control signal (heater control signal) for increasing or decreasing the current to the heaters 12, 14 based on an offset between a calculated internal resistance RVS of the Vs cell 6 and a target value or an offset between a temperature of the Vs cell 6 obtained from the internal resistance RVS and a target temperature is outputted to the heater current supply circuit 44 for controlling the value of the current supplied from the heater current supply circuit 44 to the heaters 12, 14.

If, in this heater current supply control, the heater current supply circuit 44 is constituted by a switching circuit capable of high-speed switching between the current supply and no current supply, it suffices to control a duty ratio of a driving pulse signal responsible for switching between the current supply and no current supply, whereas, if the heater current supply circuit 44 is constituted by a voltage control circuit capable of controlling an output voltage to the heaters 12, 14, it suffices if the voltage is increased or decreased based on the heater control signal from the ECU 50.

If the heater control signal is outputted in this manner, the processing proceeds to step S320 for judging whether or not a pre-set time T4, such as 500 μsec, has elapsed after start of the detection processing, to wait until lapse of the pre-set time T4. If the pre-set time T4 has elapsed, the detection processing is started at S330. The switch SW1, which has been off for the pre-set time T4, is turned on to terminate the detection processing for re-starting the operation of measuring the oxygen concentration and the NOx concentration.

In the above-described processing for detecting the internal resistance, the switch SW1 in the driving circuit 40 is turned off when the processing is started at time point t1 for stopping the supply of the small current iCP to the Vs cell 6 and the pump current control, whereupon the switch SW2 is turned on to cause the constant current to flow through the Vs cell 6 in a direction opposite to the flowing direction of the small current iCP. When the pre-set time T1 has elapsed at time point t2 since that time, the voltage Vs on the side of the porous electrode 6 at this time is set as a resistor detection voltage VS2 and the internal resistance RVS of the Vs cell 6 is detected from the offset ΔVs between the resistance detection voltage VS2 and the voltage Vs on the side of the porous electrode 6c at the time of starting the detection processing (i.e., basic detection voltage VS1), for the reason which will be now explained.

First, if the constant current for detecting the internal resistance is caused to flow through the Vs cell 6, the voltage Vs on the porous electrode 6c of the Vs cell 6 is varied not only by the internal resistance RVS of the Vs cell 6 but also by an electromotive force generated responsive to a ratio between oxygen concentration values at both the electrodes 6b and 6c. Thus, in the present embodiment, in order for the voltage Vs on the porous electrode 6c for internal resistance detection to be less susceptible to the influence of the electromotive force, a current larger than the small current iCP is caused to flow for increasing a voltage drop caused by the internal resistance RVS of the Vs cell 6.

On the other hand, since the oxygen concentration values on the electrodes 6b, 6c of the Vs cell 6 are substantially constant by pump current control and by supply of the small current iCP, respectively, the electromotive force of the Vs cell 6 also becomes substantially constant. Thus, if the constant current is caused to flow across the Vs cell 6 thereupon detecting the voltage Vs on the porous electrode 6c, that is VS2, the internal resistance RVS of the Vs cell 6 can be determined substantially correctly from this voltage value.

However, more strictly, the oxygen concentration in the first measurement chamber 20 is controlled by feedback control of the pump current and hence is fluctuated due to, for example, response delay of the control system, such that it cannot be fixed at a constant concentration value. On the other hand, the oxygen concentration in the first measurement chamber 20 is also varied depending on the temperature of the NOx sensor 2. Thus, if the internal resistance RVS is determined from the voltage Vs detected by causing the RVS detecting constant current to flow through the Vs cell 6, there might result an error, even if small, in the internal resistance RVS.

Thus, in the instant embodiment, the amount of change in the voltage Vs on the porous electrode 6c (offset ΔVs) until a pre-set time, such as 60 μsec, elapses after the time the constant current for detecting the internal resistance RVS is caused to flow through the Vs cell 6 is detected, and the internal resistance RVS is determined from this offset ΔVs. Based on this, the internal resistance RVS of the Vs cell 6 and hence the device temperature can be accurately determined even if the oxygen concentration in the first measurement chamber 20 is deviated from the target concentration.

For calculating the internal resistance RVS, the following may be employed. A map having previously stored therein the internal resistance RVS versus the offset ΔVs is provided, and the internal resistance RVS is calculated using this map.

Next, in the processing for detecting the internal resistance of the instant embodiment, if a resistance detection voltage VS2 is set at a time point t2 upon lapse of a pre-set time interval T1 (at time point t2) after start, the switches SW2 and SW3 are turned off and on, respectively, when another pre-set time, such as 40 μsec, has elapsed further at time point t3 at which the elapsed time after the start of the detection processing has reached T2. This causes the constant current to flow through the Vs cell 6 in the same direction as the small current iCP. If a further pre-set time, such as 100 μsec, has elapsed further at time point t4 at which the elasped time after the start of the detection processing has reached T3, the switch SW3 is turned off.

The result is as follows, in the instant embodiment. Since oxygen pumped from the closed space on the porous electrode 6c of the Vs cell 6 for detecting the internal resistance RVS can be returned quickly. Besides the current is caused to flow in the opposite direction to the flowing direction of iCP for reverting the internal polarized state of the Vs cell 6 to an original state, so that the closed space towards the porous electrode 6c can operate quickly as the internal reference oxygen source, as well as the Vs cell 6 can be operated quickly as the oxygen concentration measurement cell. Thus a length of time T4 which elapses after the starting of the processing until operation start of the concentration measurement can be as short as 500 μsec thus enabling the internal resistance RVS of the Vs cell 6 to be measured with high accuracy without affecting measurement of the oxygen concentration and NOx concentration.

In the above-described measurement device for measuring the oxygen concentration and the NOx concentration of the instant embodiment, the temperature of the NOx sensor 2 is detected from the internal resistance RVS of the Vs cell 6 adapted to detect the oxygen concentration in the first measurement chamber 20, and the current supply value to the heaters 12, 14 is controlled so that this temperature will be equal to the target temperature, such as 850° C. If the detected internal resistance RVS or the device temperature obtained from this internal resistance RVS deviates from the target value, the second pump current IP2 and/or the first pump current IP1 representing the results of measurement of the NOx concentration and the oxygen concentration are respectively corrected by the temperature correction value (amount) which is responsive to the offset value thereby temperature-compensating the results of measurement of the NOx concentration and the oxygen concentration. In this manner, with the measurement device for measuring the oxygen concentration and the NOx concentration of the instant embodiment, the oxygen concentration and the NOx concentration can be detected highly accurately at all times without being affected by the temperature of the NOx sensor 2.

In particular, with the instant embodiment, the NOx sensor 2 is comprised of the first pump cell 4, Vs cell 6 and the second pump cell 8, laminated in this order, and the heaters 12, 14 are laminated on both sides in the laminating directing. Moreover, if the NOx sensor 2 is projected along the laminated direction, the diffusion rate regulating layer 4d overlaps diffusion rate regulating layers 6d, 22d, and heater wires 12b, 14b of the heaters 12, 14 are arranged to interpose these diffusion rate regulating layers substantially at the mid positions. Thus, in the instant embodiment, the cells 4 to 8 can be heated efficiently, using the heaters 12, 14, by the above-described structure of the NOx sensor 2, while the gas under measurement, flowing via these diffusion rate regulating layers into the first measurement chamber 20 and the second measurement chamber 26, can also be heated efficiently. Therefore, in the instant embodiment, the temperature of each cell making up the NOx sensor 2 can be controlled more reliably to the target temperature to improve measurement accuracy of the oxygen concentration and the NOx concentration.

In the instant embodiment, current control for the first pump cell 4 is halted during measurement of the element temperature. However, if a sample-and-hold circuit is provided at an input stage to the differential amplifier AMP for sample-holding the voltage Vs on the porous electrode 6c prior to start of measurement of the device temperature, the differential amplifier AMP can be actuated by the sample-held voltage values even during measurement of the device temperature thus assuring sustained current control of the first pump cell 4.

It should be noted that any modification may be done without departing from the gist of the present invention within the disclosed concept and scope as defined by the appended claims.

What is claimed is:

1. A method for measuring an oxygen concentration and a nitrogen oxide concentration in a gas under measurement comprising:

(a) providing a NOx sensor comprising a first measurement chamber, a second measurement chamber, a first oxygen pumping cell, a second oxygen pumping cell and a heater, said first measurement chamber comprising said first oxygen pumping cell and an oxygen concentration measuring cell and communicating with the gas under measurement via a first diffusion rate regulating portion, said first oxygen pumping cell comprising an oxygen ion conductive solid electrolyte layer sandwiched between a pair of porous electrodes, said second oxygen pumping cell comprising another oxygen ion conductive solid electrolyte layer sandwiched between another pair of porous electrodes, said second measurement chamber communicating with the first measurement chamber via a second diffusion rate regulating portion, and said heater being adapted for heating the cells, said solid electrolyte layers being disposed in lamination;

wherein an oxygen concentration measurement cell for measuring the oxygen concentration of the gas under measurement supplied to the second measurement chamber is disposed between said first and second oxygen pumping cells in a laminating direction of said solid electrolyte layers;

(b) causing a current flow in said first oxygen pumping cell so that a deviation from a target value of an output voltage of the oxygen concentration measurement cell will be zero, thereby controlling an oxygen concentration in the first measurement chamber to a constant value;

(c) applying a constant voltage across said second oxygen pumping cell in a direction of pumping oxygen out of the first measurement chamber;

(d) measuring a value of a current flowing in the second oxygen pumping cell which is indicative of the nitrogen oxide concentration in the gas under measurement;

(e) simultaneously measuring a value of the current flowing in the first oxygen pumping cell which is indicative of the oxygen concentration in the gas under measurement and (f) measuring a temperature of the oxygen concentration measuring cell and correcting the current flowing in the second pumping cell based on said measured temperature.

2. The method as defined in claim 1,
wherein said heater is arranged on both sides of a laminate of said solid electrolyte layers at positions superposing said first and second oxygen pumping cells and said oxygen concentration measurement cell; and
wherein an amount of the current supplied to the heater is controlled by directly detecting internal resistance of said oxygen concentration measurement cell so that a temperature of the oxygen concentration measurement cell in the NOx sensor will be a target temperature.

3. The method as defined in claim 2, wherein measured results of the oxygen concentration and the nitrogen oxide concentration are corrected for a deviation from the target temperature of the oxygen concentration measurement cell.

4. The method of claim 1, wherein the oxygen concentration measuring cell alternatively functions as a temperature sensor of the oxygen concentration measuring cell and as an oxygen concentration measuring sensor for the gas under measurement supplied to the second measurement chamber.

5. A device for measuring an oxygen concentration and a nitrogen oxide concentration in a gas under measurement, comprising:

(a) a NOx sensor comprising a first measurement chamber, a second measurement chamber, a first oxygen pumping cell, a second oxygen pumping cell and a heater, said first measurement chamber comprising said first oxygen pumping cell and an oxygen concentration measuring cell and communicating with the gas under measurement via a first diffusion rate regulating portion, said first oxygen pumping cell comprising an oxygen ion conductive solid electrolyte layer sandwiched between a pair of porous electrodes, said second oxygen pumping cell comprising another oxygen ion conductive solid electrolyte layer sandwiched between another pair of porous electrodes, said second measurement chamber communicating with the first measurement chamber via a second diffusion rate regulating portion, and said heater being adapted for heating the cells; said solid electrolyte layers being disposed in lamination;

wherein an oxygen concentration measurement cell for measuring the oxygen concentration of the gas under measurement supplied to the second measurement chamber is disposed between said first and second oxygen pumping cells in a laminating direction of said solid electrolyte layers;

(b) pump current control means for causing a current to flow in said first oxygen pumping cell so that a deviation from a target value of an output voltage of the oxygen concentration measurement cell will be zero, thereby controlling an oxygen concentration in the first measurement chamber to a constant value;

(c) constant voltage application means for applying a constant voltage across said second oxygen pumping cell in a direction of pumping oxygen out of the second measurement chamber;

(d) nitrogen oxide concentration measurement means for measuring the nitrogen oxide concentration in the gas under measurement based on a value of a current flowing in the second oxygen pumping cell;

(e) oxygen concentration measurement means for simultaneously measuring the oxygen concentration in the gas under measurement based on a value of the current flowing in the first oxygen pumping cell (f) temperature detection means for directly detecting a temperature of the oxygen concentration measurement cell, and (g) correction means for correction of the current flowing in the second pumping cell based on a temperature as measured by the oxygen concentration measuring cell wherein said heater is arranged on both sides in a laminating direction of said solid electrolyte layers at positions superposing said first and second oxygen pumping cells and said oxygen concentration measurement cell.

6. The device of claim 4, further comprising:
heater current supply controlling means for controlling a current supplied to said heater so that the temperature of said oxygen concentration measurement cell as detected by said temperature detection means will be a target temperature.

7. The device of claim 6, further comprising:
correction means for temperature compensation of measured results of the oxygen concentration and the nitrogen oxide concentration by correcting said measured results in response to a deviation from said target temperature of the oxygen concentration measurement cell as detected by said temperature detection means.

8. The device of claim 7, wherein said temperature correction means comprises a computer which calculates an amount of temperature correction of the oxygen concentration and the nitrogen oxide concentration based on a correction map as a function of the deviation from the target temperature.

9. The device of claim 7, wherein the oxygen concentration measurement cell has a porous electrode facing the first measurement chamber.

10. The device of claim 6, wherein said temperature detection means detects the temperature of the oxygen concentration measurement cell by detecting an internal resistance of the oxygen concentration measurement cell and wherein said heater current supply controlling means controls a current supplied to said heater so that the internal resistance of the oxygen concentration measurement cell will be of a value corresponding to the target temperature.

11. The device of claim 10, further comprising a porous electrode on a side of the oxygen concentration measurement cell, said porous electrode being opposite to the first measurement chamber and closed, and part of oxygen in a closed space can be leaked out via a leakage resistance; and wherein said pump current control means causes a small amount of current to flow in said oxygen concentration measurement cell in a direction of pumping oxygen out of said first measurement space into said closed space to control an amount of current flowing in said first oxygen pumping cell so that as said closed space is caused to function as an internal oxygen reference source, an electromotive force generated across said oxygen concentration measurement cell will be of a constant value;

said temperature detection means causing periodic interruption of a connection between the pump current control means and the oxygen concentration measurement cell and during said interruption an amount of current larger than said small current for detecting the internal resistance of said oxygen concentration measurement cell is caused to flow in said oxygen concentration measurement cell in a direction opposite to that of said small current, the internal resistance of said oxygen concentration measurement cell being detected from a voltage generated across the electrodes of the oxygen concentration measurement cell during said interruption.

12. The device of claim 11, wherein said temperature detection means causes the current for detecting the internal resistance of said oxygen concentration measurement cell to flow across said oxygen concentration measurement cell in one direction and then in an opposite direction.

13. The device of claim 10, wherein the oxygen concentration measuring cell alternatively functions as a temperature sensor of the oxygen concentration measuring cell and as said oxygen concentration measuring cell.

14. The device of claim 13, wherein the oxygen concentration measuring cell is connected to a switching circuit that changes over between two modes, wherein a first mode is for supplying a constant voltage for the measuring the oxygen concentration and a second mode is for measuring said internal resistance of the oxygen concentration measurement cell.

15. The device of claim 14, wherein in said first mode, the oxygen concentration measuring cell is connected to an input of a comparator (AMP) for comparing the output voltage of the oxygen concentration cell with a target value (VC0), the comparator outputting an output signal indicative of said deviation from the target value of the output voltage of the oxygen concentration measurement cell, thereby causing said current to flow in the first oxygen pumping cell.

16. The device of claim 15, wherein said current is measured and evaluated by an electronic control unit (ECU) to determine the oxygen concentration of the gas under measurement, while said electronic control unit (ECU) determines the nitrogen oxide concentration based on the value of the current flowing in the second oxygen pumping cell.

17. The device of claim 16, wherein said electric control unit (ECU) controls said switching circuit for alternately changing over between said first and second modes.

18. The device of claim 5, wherein the oxygen concentration measurement cell comprises a solid electrolyte layer, said first measurement chamber and the second measurement chamber are made up by laminating solid electrolyte layers interposed with a small gap.

19. The device of claim 18, wherein said second diffusion rate regulating layer overlaps at least a portion of the first diffusion rate regulating layer and said oxygen concentration measurement cell is provided in a vicinity of said second diffusion rate regulating layer.

20. The device of claim 18, wherein said heater comprises two heater substrates in the form of thin plates with heater wiring embedded therein.

21. The device of claim 20, wherein the first diffusing rate regulating layer is arranged in the solid electrolyte layer of the first oxygen pumping cell so that said first diffusion rate regulating layer is disposed between said heater substrates.

22. The device of claim 5, further comprising porous electrodes of the oxygen concentration measurement cell, wherein one of said porous electrodes is disposed in the first measurement chamber.

23. The device of claim 5, wherein one of said porous electrodes of the first oxygen pumping cell is disposed in the first measurement chamber.

24. The device of claim 5, wherein said oxygen concentration measurement means comprises an electronic computing unit having a computer which calculates the oxygen concentration of the gas under measurement based on the value of the current flowing in the first oxygen pumping cell.

* * * * *